(12) United States Patent
Adam et al.

(10) Patent No.: US 7,872,141 B2
(45) Date of Patent: Jan. 18, 2011

(54) PROCESSES FOR THE MANUFACTURE OF A PYRROLIDINE-3,4-DICARBOXAMIDE DERIVATIVE

(75) Inventors: Jean-Michel Adam, Rosenau (FR); Pascal Dott, Rixheim (FR); Hans Iding, Rheinfelden (DE); Hans-Juergen Mair, Loerrach (DE); Reinhard Reents, Basel (CH); Beat Wirz, Reinach BL (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 265 days.

(21) Appl. No.: 11/959,486

(22) Filed: Dec. 19, 2007

(65) Prior Publication Data

US 2008/0214826 A1 Sep. 4, 2008

(30) Foreign Application Priority Data

Dec. 22, 2006 (EP) .................................. 06126969

(51) Int. Cl.
*C07D 401/12* (2006.01)
(52) U.S. Cl. .................................... 546/279.1
(58) Field of Classification Search ............... 546/279.1
See application file for complete search history.

(56) References Cited

U.S. PATENT DOCUMENTS

2005/0215599 A1 9/2005 Anselm et al.

FOREIGN PATENT DOCUMENTS

WO WO 2005/092881 10/2005

OTHER PUBLICATIONS

Sarmiento et al., Tetrahedron Asymm., 14, pp. 1547-1551 (2003).
Joucla et al., Bull. Soc. Chim. Fr., 579 (1988).
Tsuge et al., Bull. Chem. Soc. Jpn., 60, pp. 4091-4098 (1987).
Tsuge et al., Chem. Letters, pp. 973-976 (1986).
Joucla et al., J. Chem. Soc. Chem. Commun., pp. 1566-1567 (1985).
Hosomi et al., Chemistry Letters, pp. 1117-1120 (1984).
Katritzky et al., Tetrahedron, 50, pp. 12571-12578 (1994).
Karlsson et al., J. Chem. Soc. Perkin Trans., 1, pp. 1076-1082 (2002).
Achiwa et al., Chem. & Pharm. Bull., 33, pp. 896-898 (1985).
Cottrell et al., J. Chem. Soc. Perkins Trans., 1, pp. 1091-1097 (1991).
Carey, J.S., J. Org. Chem., 66, pp. 2526-2529 (2001).

*Primary Examiner*—Patricia L Morris
(74) *Attorney, Agent, or Firm*—George W. Johnston; Dennis P. Tramaloni; Brian C. Remy

(57) ABSTRACT

The invention is concerned with processes for the manufacture of the pyrrolidine-3,4-dicarboxamide derivative of formula (I),

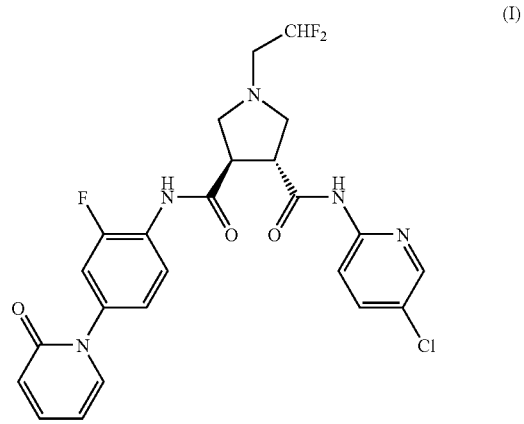

and the intermediates useful for those processes of manufacture.

8 Claims, No Drawings

PROCESSES FOR THE MANUFACTURE OF A PYRROLIDINE-3,4-DICARBOXAMIDE DERIVATIVE

PRIORITY TO RELATED APPLICATION(S)

This application claims the benefit of European Patent Application No. 06126969.2, filed Dec. 22, 2006, which is hereby incorporated by reference in its entirety.

BACKGROUND OF THE INVENTION

The invention is concerned with processes for the manufacture of a pyrrolidine-3,4-dicarboxamide derivative of formula (X)

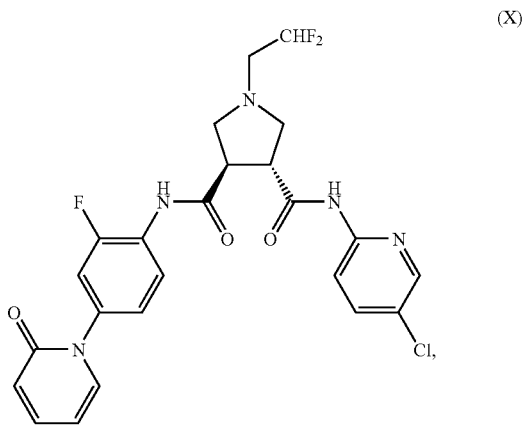

(X)

namely (3R,4R)-1-(2,2-difluoroethyl)-pyrrolidine-3,4-dicarboxylic acid 3-[(5-chloro-pyridin-2-yl)-amide]-4-{[2-fluoro-4-(2-oxo-2H-pyridin-1-yl)-phenyl]-amide}. Further, the invention is concerned with intermediates useful for those processes.

The compound of formula (X), which is disclosed in WO2005/092881, is an active compound and inhibits the coagulation factor Xa. This compound consequently influences blood coagulation, and therefore inhibits the formation of thrombin and can be used for the treatment and/or prevention of thrombotic disorders, such as amongst others, arterial and venous thrombosis, deep vein thrombosis, peripheral arterial occlusive disease (PAOD), unstable angina pectoris, myocardial infarction, coronary artery disease, pulmonary embolism, stroke (cerebral thrombosis) due to atrial fibrillation, inflammation and arteriosclerosis. This compound has potential benefit in the treatment of acute vessel closure associated with thrombolytic therapy and restenosis, e.g. after transluminal coronary angioplasty (PTCA) or bypass grafting of the coronary or peripheral arteries and in the maintenance of vascular access patency in long term hemodialysis patients. The compound of formula (X) may form part of a combination therapy with an anticoagulant with a different mode of action or with a platelet aggregation inhibitor or with a thrombolytic agent. Furthermore, the compound of formula (X) has an effect on tumor cells and prevents metastases. This compound can therefore also be used as antitumour an agent.

WO2005/092881 discloses a process for preparing the compound of formula (X). However, the process described in WO2005/092881 (in the examples) led to a low overall yield for the preparation of compound of formula (X). Also, some issues like the multiple solid additions of a paraformaldehyde/N-Bn-glycine mixture to a hot solution of diethyl fumarate for the [3+2] cycloaddition reaction, the low and varying yields of the Weinreb amidation step using the pyrophoric trimethyl aluminium, the use of large excess of alkylating agent (difluoroethyl triflate) and the moderate yield in the last step as well as the potentially unsafe combination of $K_2CO_3$ and DMSO at high temperature (for the N-arylation step) are not suitable for the up-scaling of the process.

Thus, the present invention provides improved methods for the manufacture of the compound of formula (X).

DETAILED DESCRIPTION OF THE INVENTION

Unless otherwise indicated, the following definitions are set forth to illustrate and define the meaning and scope of the various terms used to describe the invention herein.

The term "halogen" refers to fluorine, chlorine, bromine or iodine. In preferred embodiments, the halogen is fluorine, chlorine or bromine.

The term "$C_{1-5}$ alkyl", alone or in combination with other groups, refers to a branched or straight-chain monovalent alkyl radical of one to five carbon atoms. This term is further exemplified by such radicals as methyl, ethyl, n-propyl, iso-propyl, n-butyl, s-butyl, and t-butyl. The term "$C_{1-3}$ alkyl", alone or in combination with other groups, refers to a branched or straight-chain monovalent alkyl radical of one to three carbon atoms.

The term "cycloalkyl" refers to a monovalent carbocyclic radical of 3 to 10 carbon atoms. In preferred embodiments, the cycloalkyl has 3 to 6 carbon atoms, such as cyclopropyl, cyclobutyl, cyclopentyl, or cyclohexyl.

The term "alkoxy" refers to the group R'—O—, wherein R' is an alkyl. The term "lower-alkoxy" refers to the group R'—O—, wherein R' is a lower-alkyl.

The term "thio-alkoxy" refers to the group R'—S—, wherein R' is an alkyl. The term "thio-lower-alkoxy" refers to the group R'—S—, wherein R' is a lower-alkyl.

The term "fluoro-lower-alkoxy" refers to the group R"—O—, wherein R" is fluoro-lower-alkyl. Examples of fluoro-lower-alkoxy groups are $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "alkenyl" alone or in combination with other groups, stands for a straight-chain or branched hydrocarbon residue comprising an olefinic bond and 2 to 20 carbon atoms. In preferred embodiments, the alkenyl has 2 to 16 carbon atoms, more preferably 2 to 10 carbon atoms. Lower-alkenyl groups as described below also are preferred alkenyl groups. The term "lower-alkenyl" refers to a straight-chain or branched hydrocarbon residue comprising an olefinic bond and 2 to 7 carbon atoms. In preferred embodiments, the lower-alkenyl has 2 to 4 carbon atoms, such as 2-propenyl.

The term "alkinyl" alone or in combination with other groups, stands for a straight-chain or branched hydrocarbon residue comprising a triple bond and up to 20, preferably up to 16 carbon atoms. The term "lower-alkinyl" refers to a straight-chain or branched hydrocarbon residue comprising a triple bond and 2 to 7, preferably 2 to 4 carbon atoms, such as 2-propinyl. Lower-alkinyl groups can be substituted, e.g. by hydroxy.

The term "alkylene" refers to a straight chain or branched divalent saturated aliphatic hydrocarbon group of 1 to 20 carbon atoms. In preferred embodiments, the alkylene has 1 to 16 carbon atoms, more preferably up to 10 carbon atoms. Lower-alkylene groups as described below also are preferred alkylene groups. The term "lower-alkylene" refers to a straight chain or branched divalent saturated aliphatic hydrocarbon group of 1 to 7 carbon atoms. In preferred embodiments, the lower-alkylene has 1 to 6 carbon atoms, preferably 3 to 6 carbon atoms. Straight chain alkylene or lower-alkylene groups are preferred.

The term "aryl" relates to the phenyl or naphthyl group which can optionally be substituted by 1 to 5 substituents independently selected from the group consisting of lower-alkenyl, lower-alkinyl, dioxo-lower-alkylene (forming for example a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)-2-lower-alkoxy, benzyloxy-lower-alkoxy, and lower-alkyl which can optionally be substituted with halogen, hydroxy, $NH_2$, N(H, lower-alkyl) or N(lower-alkyl)$_2$. In preferred embodiments, the aryl is phenyl and is optionally substituted with 1 to 3 substituents. Preferred substituents are halogen, lower-alkoxy, fluoro-lower-alkoxy, thio-lower-alkoxy, and amino.

The term "heterocyclyl" as used herein denotes non-aromatic monocyclic heterocycles with 4 or 6 ring members, which comprise 1, 2 or 3 hetero atoms selected from nitrogen, oxygen and sulfur. Examples of suitable heterocycles are pyrrolidinyl, oxopyrrolidinyl, isoxazolidinyl, isoxazolinyl, pyrrolinyl, imidazolidinyl, imidazolinyl, pyrazolidinyl, pyrazolinyl, piperidinyl, 2-oxo-piperidinyl, 3-oxo-morpholinyl, 2-oxo-piperazinyl, 2-oxo-oxazolidinyl, 2-oxo-azetidinyl, piperazinyl, morpholinyl, pyranyl, tetrahydropyranyl, 4,5-dihydro-oxazolyl, 4,5-dihydro-thiazolyl. Preferred heterocycles are, morpholinyl, 3-oxo-morpholinyl, 2-oxo-piperazinyl and 2-oxo-piperidinyl. A heterocyclyl group may have a substitution pattern as described earlier in connection with the term "aryl".

The term "heteroaryl" refers to a aromatic 5 to 6 membered monocyclic ring or 9 to 10 membered bicyclic ring which can comprise 1, 2 or 3 atoms selected from nitrogen, oxygen and sulphur, such as furyl, pyridyl, pyridazinyl, oxo-pyridazinyl, pyrimidinyl, 2-oxo-pyridinyl, 2-oxo-pyrimidinyl pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzoimidazolyl, indolyl, and indazolyl. Preferred heteroaryl groups are 2-oxo-pyridinyl, 2-oxo-pyrimidinyl, pyridinyl, and indolyl. A heteroaryl group may have a substitution pattern as described earlier in connection with the term "aryl". In preferred embodiments the heteroaryl is substituted with halogen, lower-alkyl, lower-alkoxy or CN.

In reference to a particular group or molecule, the term "substituted" refers to the fact that at least one of the hydrogen atoms of that group or molecule is replaced by some other substituent.

General Synthetic Processes

According to the present invention, the Compound of formula (X) is manufactured as follows:

I Enzymatic Route A

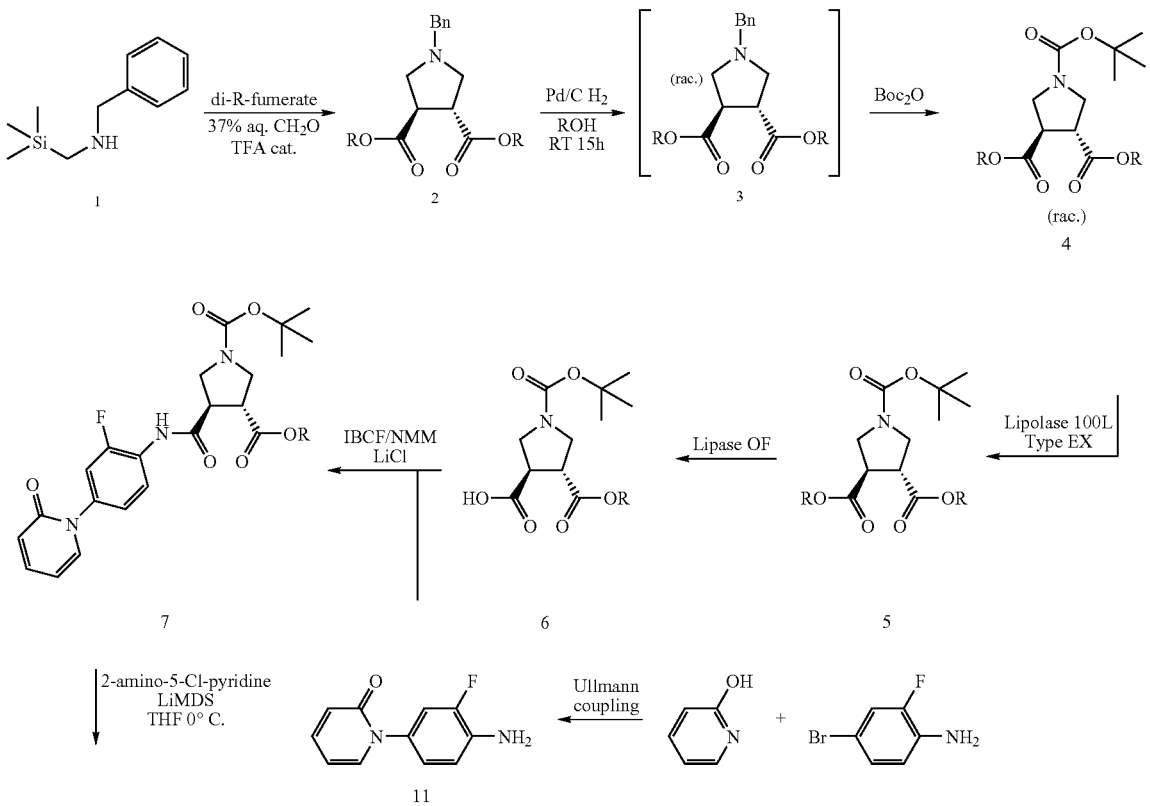

Scheme 1

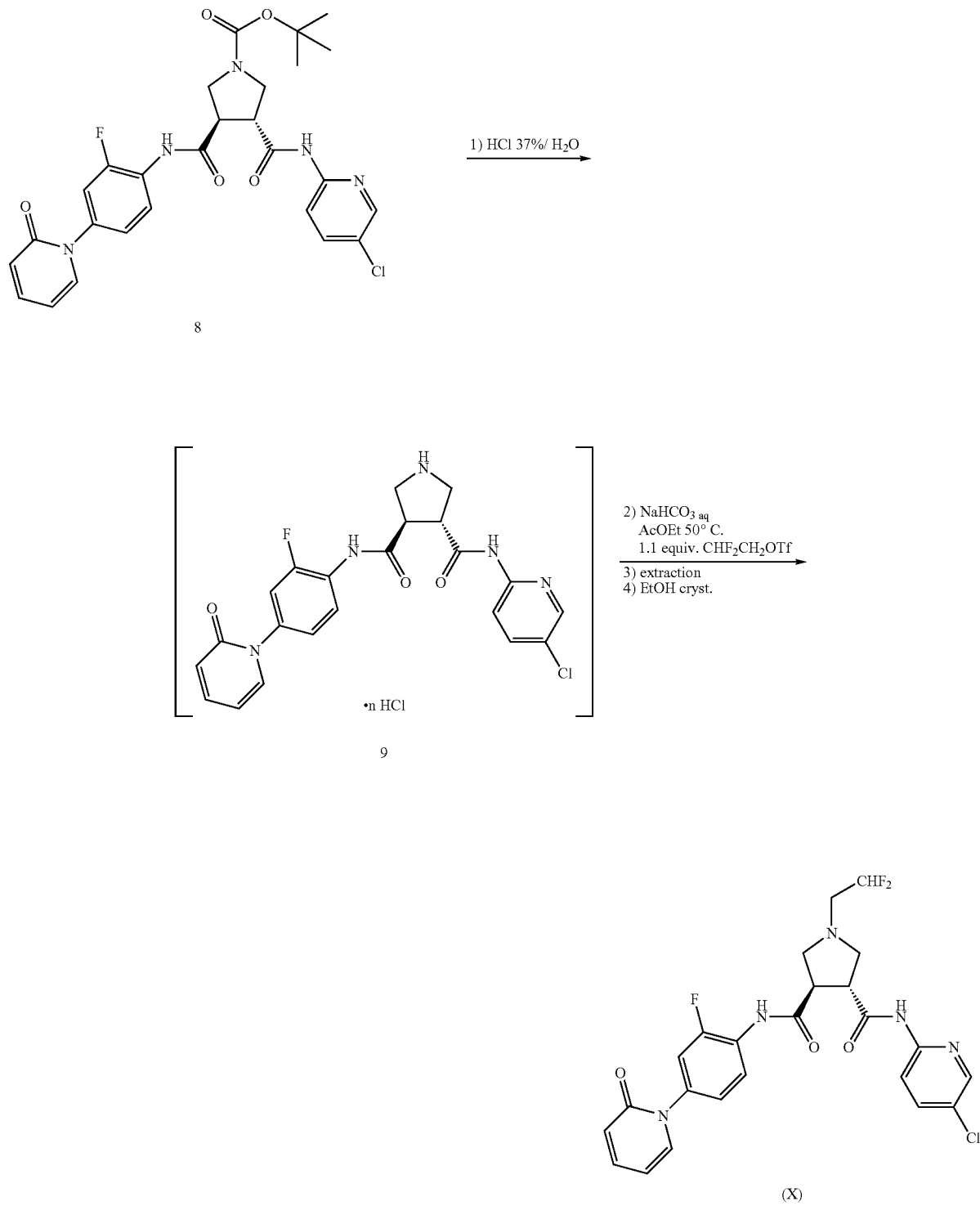
In scheme 1, R means a $C_{1-5}$ alkyl or a $C_{1-3}$ alkyl substituted by one or more substituents selected from the group consisting of hydroxyl, methoxy, ethoxy and halogen. Compounds of formula (6) can be hydrates. Especially, hydrates of the Compounds of formula (6), wherein R is Et, (6') can be easily isolated as the corresponding crystalline hydrate (6').

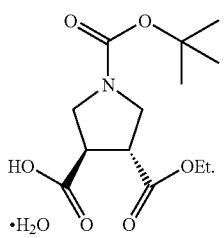

(6')

This route comprises the following steps:
1. A dipolar [3+2] cycloaddition between an in situ generated azomethine ylide to provide the benzyl protected pyrrolidine 2.
2. The debenzylation of pyrrolidine 2 to provide 3.
3. The Boc protection of 3 to provide the racemic di-ester 4.
4. The enzymatic resolution where the (S,S)-enantiomer is hydrolyzed and washed out providing (R,R)-diester 5.
5. A selective monohydrolysis providing the (R,R)-mono acid 6.
6. An amide coupling with aniline 11 giving amide ester 7.
7. A basic amidation with 2-amino-5-chloropyridine providing the bis-amide 8.
8. A Boc deprotection providing pyrrolidine 9.
9. An alkyation providing the difluoroethyl amine 10.

I-1. Cycloaddition Step

As found in the literature (Rodriguez Sarmiento et al., *Tetrahedron: Asymm.* 2003, 1547-1551; M. Joucla, J. Mortier, *Bull. Soc. Chim. Fr.* 1988, 579; O. Tsuge, S. Kanemasa, M. Ohe, S. Takenaka, *Bull. Chem. Soc. Jpn.* 1987, 4079; O. Tsuge, S. Kanemasa, M. Ohe, S. Takenaka, *Chem. Letters* 1986, 973; M. Joucal, J. Mortier, *J. Chem. Soc. Chem. Comm.* 1985, 1566.), the cycloaddition can be performed by reaction of the fumaric acid diester with N-benzylglycine and formaldehyde (paraformaldehyde). The cycloaddition can also be performed by reacting fumaric acid diester with an azomethine ylide precursor, such as a N-(alkoxymethyl) or a N-(benzotriazol-methyl) derivative of N-benzyl-trimethylsilylmethyl amine 1 generally under acid/Lewis acid catalysis or thermal condition (Hosomi et al., *Chemistry Letters* 1984, 1117; Katritzky et al., *Tetrahedron* 1994, 12571; Karlsson and Horberg, *J. Chem. Soc. Perkin Trans.* 1 2002, 1076; Kazuo et al., *Chem. & Pharm. Bull.* 1985, 896; I. F. Cottrell, D. Hands, D. J. Kennedy, K. J. Paul, S. H. B. Wright, K. Hoogsteen, *J. Chem. Soc. Perkin Trans.* 11991, 1091; J. S. Cavey, *J. Org. Chem.* 2001 2526; C. Savarin, "Organic Process Research and Development", Scientific Update conference proceedings, Nice, Mar. 30, 2006). The ylide precursor is generally isolated and water is generally excluded from the reaction mixture to prevent quench of the in-situ generated ylide.

It was however found that reacting N-benzyl-trimethylsilylmethyl amine 1 with aqueous formaldehyde provided an azomethine ylide precursor which could be directly used for the cycloaddition with the fumaric acid diester without prior drying. Indeed, under suitable conditions, competition between the cycloaddition of the generated ylide with the fumarate and quench of the ylide with water is in favor of the cycloaddition, providing excellent yield of the cycloadduct (N-methyl-N-benzylamine is detected in the crude reaction mixture which is indicative of the competitive ylide quench with water). This provides a simple process from N-benzyl-trimethylsilylmethyl amine 1 and aqueous formaldehyde and avoids the isolation of the ylide precursor.

So, first N-benzyl-trimethylsilylmethyl amine 1 is dissolved in a suitable solvent such as THF, dioxane, toluene, ethyl acetate and DME. THF is preferred. Aqueous formaldehyde, (preferably a concentrated solution, typically a ca 36% solution, at least one equivalent) is added at room temperature (it is detrimental to heat this solution in the absence of fumaric acid diester since ylide generation might take place followed by ylide quench with water).

The resulting mixture is reacted with the fumaric acid diester under for instance purely thermal conditions, preferably over 50° C.

The reaction with the fumaric acid diester can also be performed at lower temperature (for example at room temperature), in this case, the reaction may need to be catalyzed by the addition of a suitable acid, such as trifluoro acetic acid, methanesulfonic acid, p-toluenesulfonic acid, hydrochloric acid, sulfuric acid, phosphoric acid, triflic acid, formic acid and acetic acid. Trifluoro acetic acid, methanesulfonic acid, p-toluenesulfonic acid, hydrochloric acid, sulfuric acid or phosphoric acid is preferred. Trifluoroacetic acid is more preferred. The acid catalyzed reactions may also be performed at elevated temperatures, for example in refluxing THF.

The preferred conditions comprise the addition of concentrated formaldehyde solution (at least one equivalent, preferably between 1 and 1.5 equivalent) to a solution of N-benzyl-trimethylsilylmethyl amine 1 in THF. The cycloaddition is performed by reacting at room temperature the resulting reaction mixture with a THF solution of fumaric acid diester and catalytic amounts of trifluoroacetic acid (preferably lower than 1 equivalent, more preferably between 1 and 5 mol %). Under these conditions, the cycloaddition part can be performed between 0° C. and 60° C., preferably between 20° C. and 60° C., more preferably at room temperature.

Other orders of addition are possible, for example addition of the N-benzyl-trimethylsilylmethyl amine 1 to a mixture of fumaric acid diester, trifluoroacetic acid, and formaldehyde in THF or addition of formaldehyde to a mixture of N-benzyl-trimethylsilylmethyl amine 1, trifluoroacetic acid and fumaric acid diester in THF, or the corresponding inverse addition modes.

An alternative process consists in adding a mixture of N-benzyl-trimethylsilylmethyl amine 1 and formaldehyde to a hot mixture of fumaric acid diester (for example in THF at 40° C. to refluxing temperature, preferably at reflux). Mixing N-benzyl-trimethylsilylmethyl amine, formaldehyde and trifluoroacetic acid in the absence of fumaric acid diester is not preferred since the ylide will be generated and quenched by water.

Under the suitable conditions, the purity of the cycloadduct is sufficient for it to be introduced directly in the next step. However, if necessary, the cycloadduct can be purified by methods known by the person skilled in the art, for instance distillation, chromatography or salt formation.

I-2. and 3. De-benzylation-Boc Protection

Compound 2 can be de-benzylated under standard conditions known by the person skilled in the art, comprising for example hydrogenolysis in the presence of a catalyst, such as palladium on carbon or palladium hydroxide on carbon. The hydrogenolysis can be performed in a suitable solvent, such as ethanol, THF, ethyl acetate and acetic acid. Ethanol is preferred. Acids, such as hydrochloric acid can be added but the reaction is preferably performed on the free base. The deprotected amine 3 can be Boc protected to provide compound 4 by standard conditions known by the person skilled in the art. Preferred conditions comprise reacting compound 3 with Boc₂O in a solvent, such as ethanol, THF, MTBE, ethyl acetate and toluene, preferably in ethanol or THF, at a temperature between 0° C. and 100° C., preferably between 20° C. and 40° C., more preferably at room temperature. In order to destroy excess Boc₂O, the crude product can be reacted with DMAP or glycine, preferably with DMAP, in aqueous THF.

Under suitable conditions (see experimental part), the crude product is of suitable purity for it to be introduced directly in the next step. However, if necessary, it can be purified by methods known by the person skilled in the art, for instance by distillation or chromatography.

I-4. and 5. Enzymatic Resolution/Monohydrolysis

1. Enantioselective enzymatic hydrolysis of trans-racemic N-Boc-pyrrolidine-3,4-dicarboxylic acid diester (4) as outlined in Scheme 2 and 2. selective monohydrolysis of the retained (R,R)—N-Boc-pyrrolidine-3,4-dicarboxylic acid diester (5) in an aqueous buffer according to Scheme 2.

The enantioselective hydrolysis is carried out by contacting an enzyme with the diester substrate (4) emulsified in an aqueous buffer by vigorous stirring until the retained diester (5) has reached a high enantiomeric excess (>50% conversion).

In addition to the resolution of the diethyl ester 4 with the specialty enzyme ESP-ESL 1199 (Diversa Corporation) described in literature (Rodriguez Sarmiento, Wirz & Iding (2003) Tetrahedron: Asymm. 14, 1547-1551), further enanti-

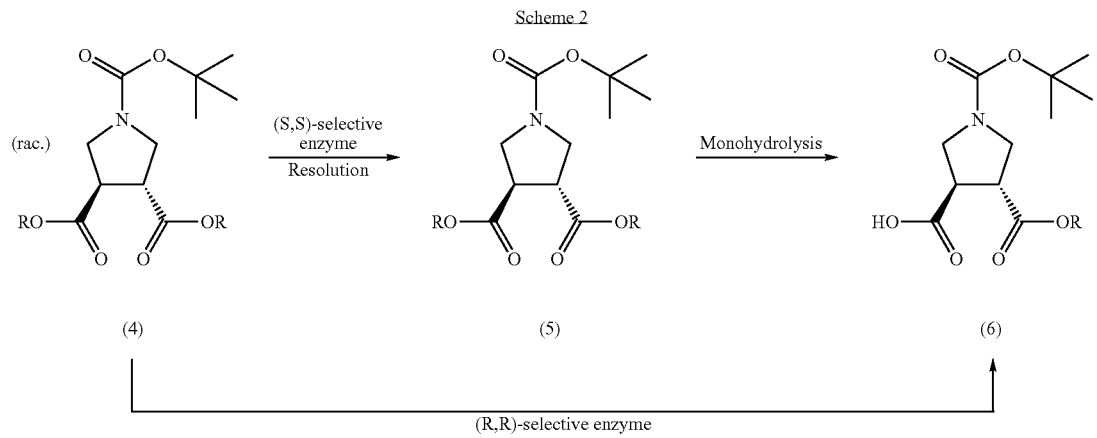

In scheme 2, R is a $C_{1-5}$ alkyl or a $C_{1-3}$ alkyl substituted by one or more substituents selected from the group consisting of hydroxyl, methoxy, ethoxy and halogen. Compounds of formula (6) can be hydrates. Especially, Compounds of formula 6, wherein R is Et, can be easily isolated as the corresponding hydrate 6'.

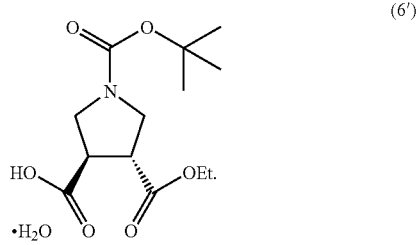

(R,R)—N-Boc-pyrrolidine-3,4-dicarboxylic acid monoesters of formula (6) are used as intermediates to prepare a compound of formula (X). A preferred $C_{1-5}$ alkyl for R is methyl, ethyl or n-propyl, more preferably methyl or ethyl, especially ethyl. Diesters of formula (4) are prepared as described before.

The intermediates (6) can be prepared through chemoenzymatic procedures based on kinetic racemic resolution described below.

oselective enzymes could be found when applying appropriate reaction conditions: Esterase NE09 (Thermogen purchased via Selectchemie AG [Etzelstrasse 42, P.O. Box 772, CH-8038 Zütrich, Switzerland]), lipase from *Rhizopus oryzae* and lipase from *Thermomyces lanuginosus*. Preferred are the lipases from *Rhizopus oryzae*—a commercial preparation of which is Lipase D from Amano Enzymes Inc. (Nagoya, Japan)—and from *Thermomyces lanuginosus*, most preferred is lipase from *Thermomyces lanuginosus*, a commercially available representant of which is Lipolase 100L Type EX from Novozymes (Bagsvaerd, Denmark), a cheap commodity enzyme, which turned out to be more robust with respect to substrate quality than Esterase 1199.

Suitable buffers are the conventional buffers commonly used in biochemistry in the range of pH 5-10, preferably 6-9. In the course of the reaction the pH of the reaction mixture is kept constant at the selected value by the addition of a base, preferentially NaOH or KOH-solution.

In the case of Lipolase 100L Type EX, the use of phosphate buffer (e.g. pH7) in the presence of a non-polar organic solvent such as n-heptane (e.g. 5% v/v) or ammonium chloride (e.g. 0.5M) positively influences selectivity (E≧25). A higher concentration of phosphate buffer (e.g. 100 mM) strongly enhances the enzyme activity which in turn allows a reduction in temperature for the sake of increased enantioselectivity. The substrate concentration may range from 1-20% w/w, preferably from 5-15% w/w.

All enzymes might be applied at a lower temperature (0-25° C.) in order to enhance the enantioselectivity. The activity of the enzyme can be increased by working at a higher temperature however at the cost of selectivity. As an alternative, the enzymes may be used in immobilized form. After termination of the reaction, the diester product is worked up conventionally by extraction.

The retained, enantiomerically pure (typically obtained in over 99% e.e.) (R,R)-diester (5) is then monohydrolyzed to enantiomerically pure (R,R)-monoester (6) using the commodity enzyme Lipase OF from *Candida cylindracea* (*C. rugosa*; Meito Sangyo; Tokyo, Japan) as described in the literature (Rodriguez Sarmiento, Wirz & Iding (2003) Tetrahedron: Asymm. 14, 1547-1551). At a higher, technically more relevant substrate concentrations of 5-15% the formation of diacid was more pronounced, but the performance of the enzyme could be improved:

The selectivity of Lipase OF at higher substrate concentrations was triggered by adding a sugar (e.g. 1M D-glucose) to the aqueous buffer. For product isolation with a technically relevant solvent as extractant (e.g. ethyl acetate) the pH of the aqueous phase containing the product monoester and the diacid side product was set to 4.0-4.5.

Optionally, the (R,R)-monoester 6 might be synthesized directly from diester 4 by enantioselective monohydrolysis using a highly (R,R)-selective enzyme.

I-6. First Amide Coupling

Suitable conditions for the reaction of compound of formula 6 (as anhydrous form) and compound 11 to provide amide ester 7 is well known by the person skilled in the art. Such reactions can be carried out in a suitable solvent, such as dichloromethane, DMF, acetonitrile, THF, NMP and DMA, preferably in THF or acetonitrile, more preferably in THF in the presence of a suitable coupling agent, such as EDC, DIC, DCC, CDI, TBTU, HBTU, EEDQ, CIP, HOBt, HATU, PyBOP, PyBrOP, BOP, BOP-Cl and TFFH, at a suitable temperature which can be chosen in the range of −20° C. to 120° C. Additional reaction conditions may involve the use of coupling agents like CDMT (2-Chloro-4,6-dimethoxy-[1,3,5]triazine), trichlorotriazine or their corresponding N-methylmorpholine adduct (i.e.: 4-(4,6-dimethoxy-[1,3,5]triazin-2-yl)-4-methyl-morpholinium chloride).

Alternatively, the acid 6 might be activated by the use of an alkyl or aryl chloroformate, preferably an alkyl chloroformate, preferably a lower alkyl chloroformate, more preferably isobutyl chloroformate, in a solvent, such as dichloromethane, DMF, acetonitrile, THF, NMP and DMA, preferably in DMF, THF or acetonitrile, more preferably in THF, in combination with a base such as triethylamine, N-methylmorpholine, N,N-dimethylaniline and collidine, preferably in combination with N-methylmorpholine or collidine, more preferably in combination with N-methylmorpholine. The activation is performed at a suitable temperature chosen between −50° C. to 50° C., preferably between −20° C. and 40° C., more preferably between −10° C. and 20° C. The chloroformate can be added to a mixture of acid 6 and the suitable amine or by inverse addition of a mixture of the amine and acid 6 to the chloroformate, preferably the latter order of addition. The activated acid is then reacted with the aniline 11 at a temperature chosen from 0° C. to 120° C., preferably between 20° C. and 60° C., preferably between 50° C. and 60° C. It was found that the reaction rate can be dramatically increased by addition of an inorganic salt, such as lithium chloride which allows the reaction to be easily performed at room temperature. The lithium chloride most probably activate the mixed anhydride by complexation of the 1,3-dicarbonyl fragment.

Alternatively, the acid can be converted to the corresponding acid chloride prior to reaction with aniline 11 under conditions well known by the persons skilled in the art. Preferred conditions comprise the activation with $SOCl_2$, $OPCl_3$, oxalyl chloride or tetramethyl keteneiminium chloride, preferably oxalyl chloride. Depending on the reagent used, it might be necessary to quench the generated hydrochloric acid by use of a tertiary base to avoid Boc deprotection.

I-7. Second Amide Coupling

Amide ester 7 can be directly converted to the bis-amide 8 with 2-amino-5-chloropyridine, under conditions known by the person skilled in the art, in the presence of a trialkyl alane or dialkylaluminium chloride or alkyl aluminium dichloride, preferably in the presence of a trialkyl alane in a suitable solvent, such as THF, dioxane, DME and toluene, preferably in dioxane or toluene, more preferably in toluene, at a suitable temperature chosen in the range from −10° C. to 120° C., preferably between 50° C. and 120° C., more preferably between 90° C. and 110° C.

Alternatively, amide ester 7 can be directly converted to the bis-amide 8, under conditions known by the person skilled in the art, in the presence of a strong base such as NaH, LiH, KH, LDA, LiHMDS, KHMDS, NaHMDS, LiOtBu, KOtBu, NaOtBu, lithium t-amylate, potassium t-amylate and sodium t-amylate, preferably in the presence of LiHMDS, LDA or lithium t-amylate, more preferably in the presence of LiHMDS or lithium t-amylate, even more preferably in the presence of LiHMDS, in a suitable solvent, such as THF, dioxane, DME, toluene or DMSO, preferably in THF, dioxane or DME, more preferably in THF, at a suitable temperature which can be chosen e.g. between −20° C. and 80° C. Preferred conditions comprises the use of LiHMDS in THF at a temperature between −10° C. to 60° C., preferably between 0° C. and 40° C., more preferably between 0° C. and room temperature.

After work-up of the reaction mixture, the product 8 is best crystallized from ethanol.

Alternatively, the bis-amide 8 can be obtained from amide ester 7 via saponification to the corresponding acid amide followed by coupling with 5-chloro-2-amino-pyridine. Conditions to be used for the saponification of the ester are well known by the person skilled in the art. The same holds for the coupling with 5-chloro-2-amino-pyridine, general conditions for this can also be found in the description of the present invention.

I-8. and 9. Boc-Deprotection—Alkylation

The bis-amide 8 can be Boc-deprotected under conditions well known by the person skilled in the art in a suitable solvent, such as toluene, ethanol, ethyl acetate, acetone, dioxane, THF, isopropanol and water, preferably in THF, isopropanol or water, more preferably in water, in the presence of an acid, such as methanesulfonic acid, p-toluenesulfonic acid, phosphoric acid, HBr, sulfuric acid, triflic acid, trifluoro acetic acid and hydrochloric acid, preferably in the presence of trifluoroacetic acid or hydrochloric acid, more preferably in the presence of hydrochloric acid.

The deprotected amine 9 can be isolated as a salt (for example: when performing the Boc deprotection with HCl in iPrOH the hydrochloride salt 9 n HCl, with n typically between 1.8 and 2.6, could be isolated by filtration) or as free base by work-up known by the person skilled in the art. However, due to the water solubility of the free base, the product is preferably directly introduced in the following step, i.e. the alkylation step. Under suitable reaction conditions, the crude reaction mixture can be directly introduced in the next step (see vide infra).

Amine 9 can be alkylated in a suitable solvent, such as acetonitrile, THF, dioxane, dichloromethane, DMF, DMSO, DMA, NMP and ethyl acetate, preferably in THF, DMSO, dichloromethane or acetonitrile, more preferably in dichloromethane or acetonitrile, further more preferably in acetonitrile, with an alkylating agent, such as a 2,2-difluoroethyl halogenide (iodide, bromide, chloride), 2,2-difluoroethyl tosylate, 2,2-difluoroethyl methanesulfonate, 2,2-difluoroethyl n-nitrobenzenesulfonate (n=2, 3 or 4) or 2,2-difluoroethyl triflate, preferably with 2,2-difluoroethyl n-nitrobenzenesulfonate (n=2, 3, 4) or 2,2-difluoroethyl triflate, more preferably with 2,2-difluoroethyl 3-nitrobenzenesulfonate or 2,2-difluoroethyl triflate, at a suitable temperature, chosen, e.g. from 20° C. to 130° C., in the presence of a suitable base, such as triethylamine, ethyl-diisopropylamine, collidine, pyridine, lutidine, $Na_2CO_3$, $NaHCO_3$, $K_2CO_3$ and $Cs_2CO_3$, preferably in the presence of ethyl-diisopropylamine or collidine, more preferably in the presence of ethyl-diisopropylamine. Preferred conditions for the alkylation of the free base comprise reaction with 2,2-difluoroethyl-3-nitrobenzensulfonate in acetonitrile at a temperature between 20° C. and 80° C., preferably between 50° C. and 80° C., more preferably in refluxing acetonitrile in the presence of a tertiary amine, such as ethyl-diisopropylamine. Other preferred conditions for the alkylation of amine 9 comprises reaction with 2,2-difluoroethyl triflate in THF, acetonitrile, ethyl acetate or dichloromethane, preferably in THF, acetonitrile or dichloromethane, more preferably in dichloromethane, at a temperature between −10° C. and 80° C., preferably between 0° C. and 50° C., more preferably between 0° C. and room temperature, in the presence of a tertiary amine, such as ethyl-diisopropylamine.

The deprotected amine, as acid salt can be alkylated under similar conditions described above for the free base, the latter being generated in situ by the action of a suitable base. However, if the counter anion part of the salt can also act as a nucleophile (like a chloride ion) and react in a competing manner with the alkylating agent, it will be necessary to introduce an excess of alkylating agent. In this case, it might be preferable to work under biphasic aqueous/organic solvent conditions. Under suitable conditions, the counter anion can be segregated in the aqueous phase and is not able to react with the alkylating agent present in the organic phase. The free amine generated in-situ by the use of a suitable base, although partly water soluble, will be continuously extracted in the organic phase where it will be alkylated by a suitable alkylating agent.

Most preferred conditions for the Boc-deprotection/biphasic alkylation comprises Boc deprotection in ethyl acetate, THF, isopropanol or water, preferably in THF, isopropanol or water, more preferably in water. The alkylation step is performed from the crude Boc-deprotection reaction mixture in the presence of water, as well as a suitable base, such as ethyl-diispropylamine, $Na_2CO_3$, $NaHCO_3$, $KHCO_3$, $K_2CO_3$, NaOH, KOH, or a mixture thereof, such as a mixture of ethyl-diispropylamine and NaOH (or KOH), a mixture of ethyl-diispropylamine and $NaHCO_3$ (or $KHCO_3$), a mixture of $NaHCO_3$ and NaOH (KOH) and a mixture of $KHCO_3$ and KOH (or NaOH), more preferably in the presence of $NaHCO_3$, as well as in the presence of an additional organic solvent, such as ethyl acetate, isopropyl acetate, 2-methyl-THF, MTBE and toluene, preferably in the presence of ethyl acetate, isopropyl acetate or 2-methyl-THF, more preferably in the presence of ethyl acetate, as well as in the presence of an alkylating agent, such as 2,2-difluoroethyl n-nitrobenzenesulfonate (n=2, 3, 4) and 2,2-difluoroethyl triflate, preferably in the presence of difluoroethyl 3-nitrobenzenesulfonate or 2,2-difluoroethyl triflate, more preferably in the presence of 2,2-difluoroethyl triflate, at a suitable temperature chosen between 0° C. and 100° C., preferably between 20° C. and 50° C.

Under optimal conditions, it is possible to use equivalent amounts or only a slight excess of alkylating agent (see the experimental description of the reaction and similar examples).

II Alternative Route to Obtain Boc-Pyrrolidine Intermediate 4 by Cycloaddition/Boc Protection An alternative process for the preparation of the Boc-pyrrolidine intermediate 4 consists of a [3+2] cycloaddition from trimethylsilymethyl-amine 12 providing the aminal 13 which can be directly converted to the desired Boc-pyrrolidine or liberated to the pyrrolidine 3 which as described above is easily Boc protected to provide 4. This sequence obviates the de-benzylation step and is also more atom efficient.

Scheme 3

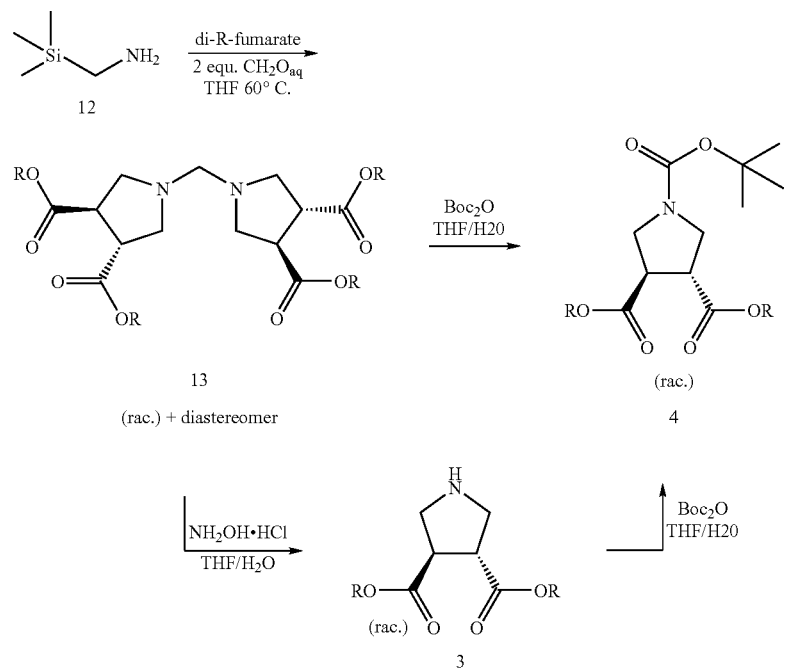

In scheme 3, R is $C_{1-5}$ alkyl or $C_{1-3}$ alkyl substituted by one or more substituents selected from the group consisting of hydroxyl, methoxy, ethoxy and halogen.

II-1. New [3+2] Cycloaddition

The [3+2] cycloaddition between trimethylsilymethylamine and fumaric acid diester can be performed under conditions similar to the cycloaddition described for the conversion of 1 to 2. However, under identical conditions, low to moderate yields are obtained. Critical to the best outcome of the reaction is the amount of formaldehyde used. The reaction is best performed using an excess of formaldehyde, over 1.3 equivalents, preferably between 1.5 and 3 equivalents, more preferably 2 equivalents. Although activation by acid catalysts as described for the conversion of 1 to 2 is possible, the reaction is best performed under pure thermal conditions at a temperature chosen form 40° C. to 120° C., preferably between 50° C. and 80° C., more preferably between 55° C. and 65° C., in a solvent, such as THF, dioxane, NMP, DMSO, DMA, DME, DMF, ethyl acetate and toluene, preferably in THF, dioxane, DMSO or toluene, more preferably in THF or dioxane.

II-2. Boc Protection

The aminal can be directly converted to the Boc protected pyrrolidine 4 by reaction with $Boc_2O$ in a water/organic solvent mixture. During the reaction, the aminal is hydrolyzed in situ to the corresponding pyrrolidine 3, which then reacts with $Boc_2O$ to give 4. The reaction is best performed in a mixture of water and an organic solvent, such as THF, dioxane, toluene, ethyl acetate, MTBE, isopropyl acetate, acetone and dichloromethane. Preferred organic solvents are THF, dioxane, toluene, ethyl acetate, MTBE or isopropyl acetate, more preferably ethyl acetate, MTBE or THF. The reaction can also be performed in the presence of a base, such as $NaHCO_3$, $KHCO_3$, triethylamine, $Na_2CO_3$ and $K_2CO_3$. A preferred base is $NaHCO_3$ or $KHCO_3$, especially $NaHCO_3$. Alternatively, the aminal can be reacted with hydroxylamine hydrochloride, for instance in a water/organic solvent mixture to provide pyrrolidine 3 after work-up. This reaction is optionally performed in the presence of base, such as $NaHCO_3$, $KHCO_3$, triethylamine, $Na_2CO_3$ and $K_2CO_3$. A preferred base is $NaHCO_3$ or $KHCO_3$, especially $NaHCO_3$. If necessary the Boc-pyrrolidine 4 can be purified by methods known by the person skilled in the art, e.g., chromatography or distillation.

III Alternative Route to Convert Amide Ester 7 to Compound (X) by Deprotection/Free Base Formation/Alkylation/Amide Formation.

Scheme 4

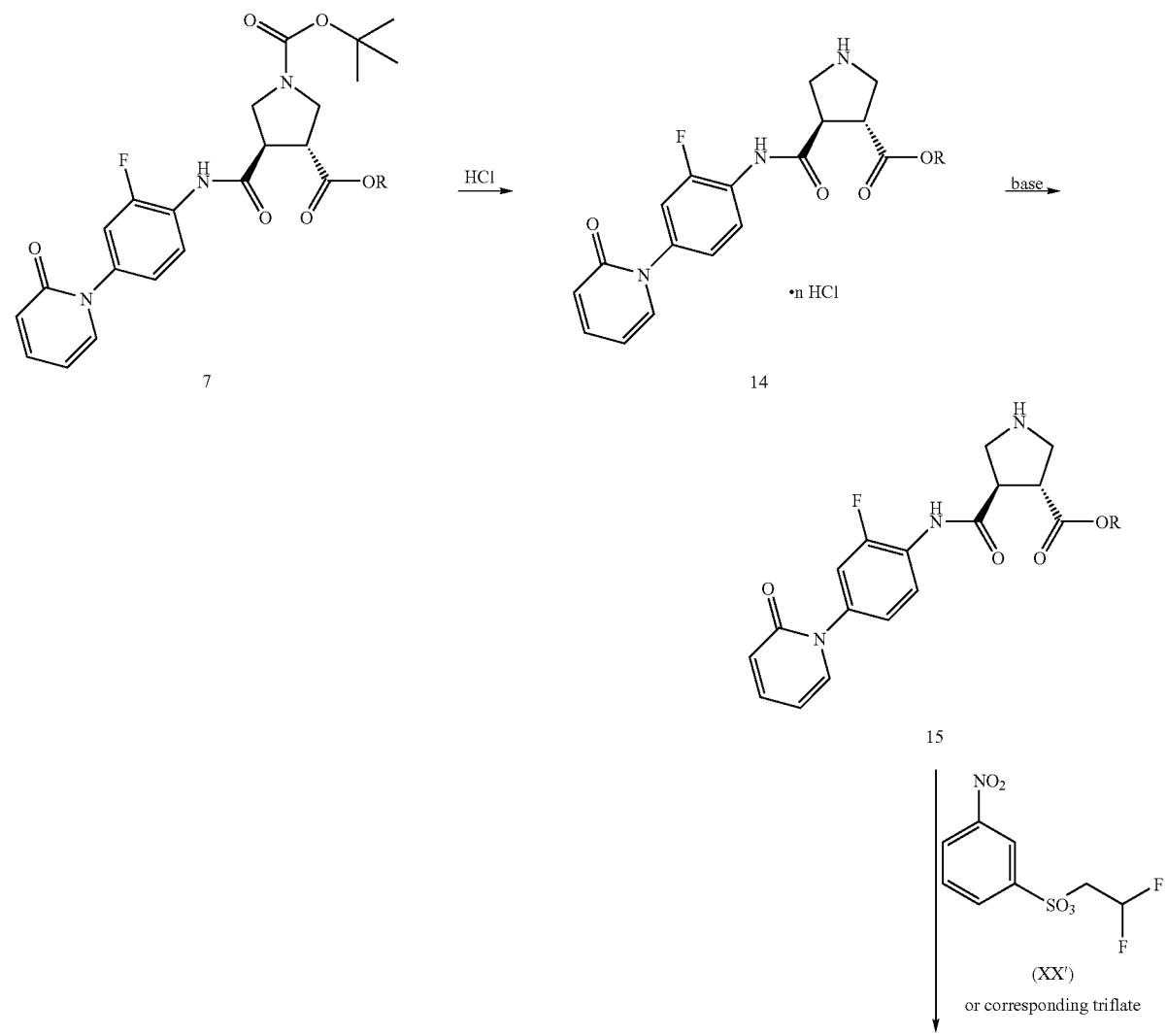

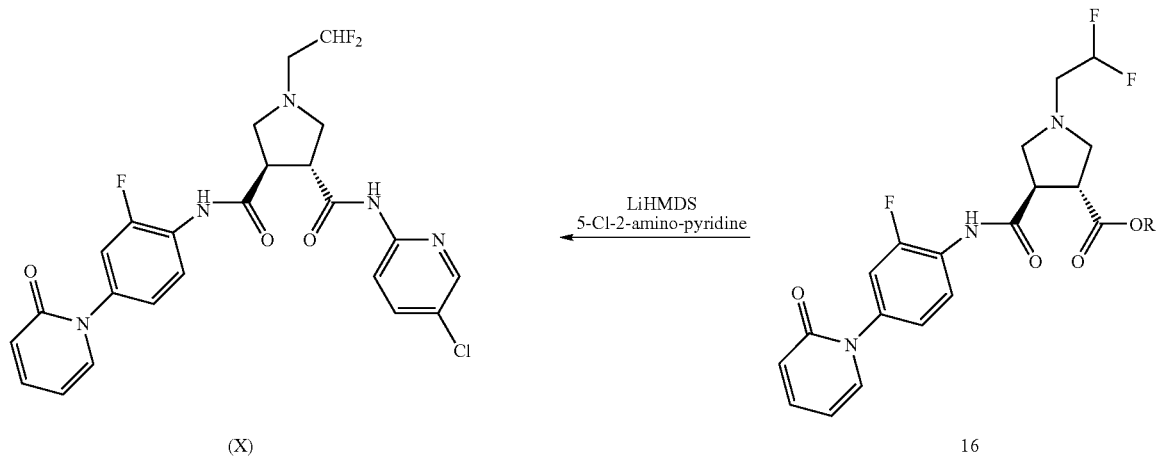

In scheme 4, R is $C_{1-5}$ alkyl or $C_{1-3}$ alkyl substituted by one or more substituents selected from the group consisting of hydroxyl, methoxy, ethoxy and halogen.

An alternative process for the conversion of amide ester 7 to compound (X) consists in a reaction sequence involving, a) Boc deprotection, b) alkylation (preferably on the free base), and second amide formation.

Boc deprotection is performed under conditions known by the person skilled in the art. The deprotected pyrrolidine can be isolated as hydrochloride salt or as free base by the appropriate work-up. For instance, hydrochloride 14, wherein R is Et, can be transformed into the free amine 15 by reaction with $NH_3$ (for example as a solution in ethanol) in a suitable solvent. Suitable solvent comprises ethanol or a mixture of ethanol and an organic solvent, such as ethyl acetate, toluene, MTBE, acetone, isopropyl acetate, diisopropyl ether and THF, preferably ethyl acetate.

The free amine 15 is then alkylated by conditions already described vide supra for analogous substrates. Preferred conditions comprises the use of difluoroethyl triflate and difluoroethyl 3-nitrobenzenesulfonate in a suitable solvent or solvent mixture, in the presence of a suitable base.

IV Enzymatic Route B

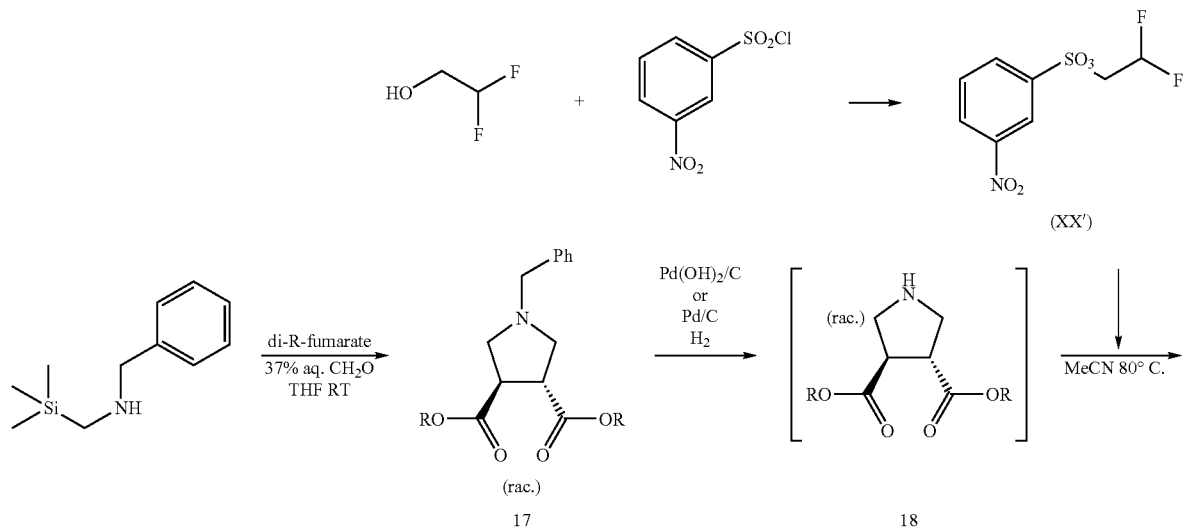

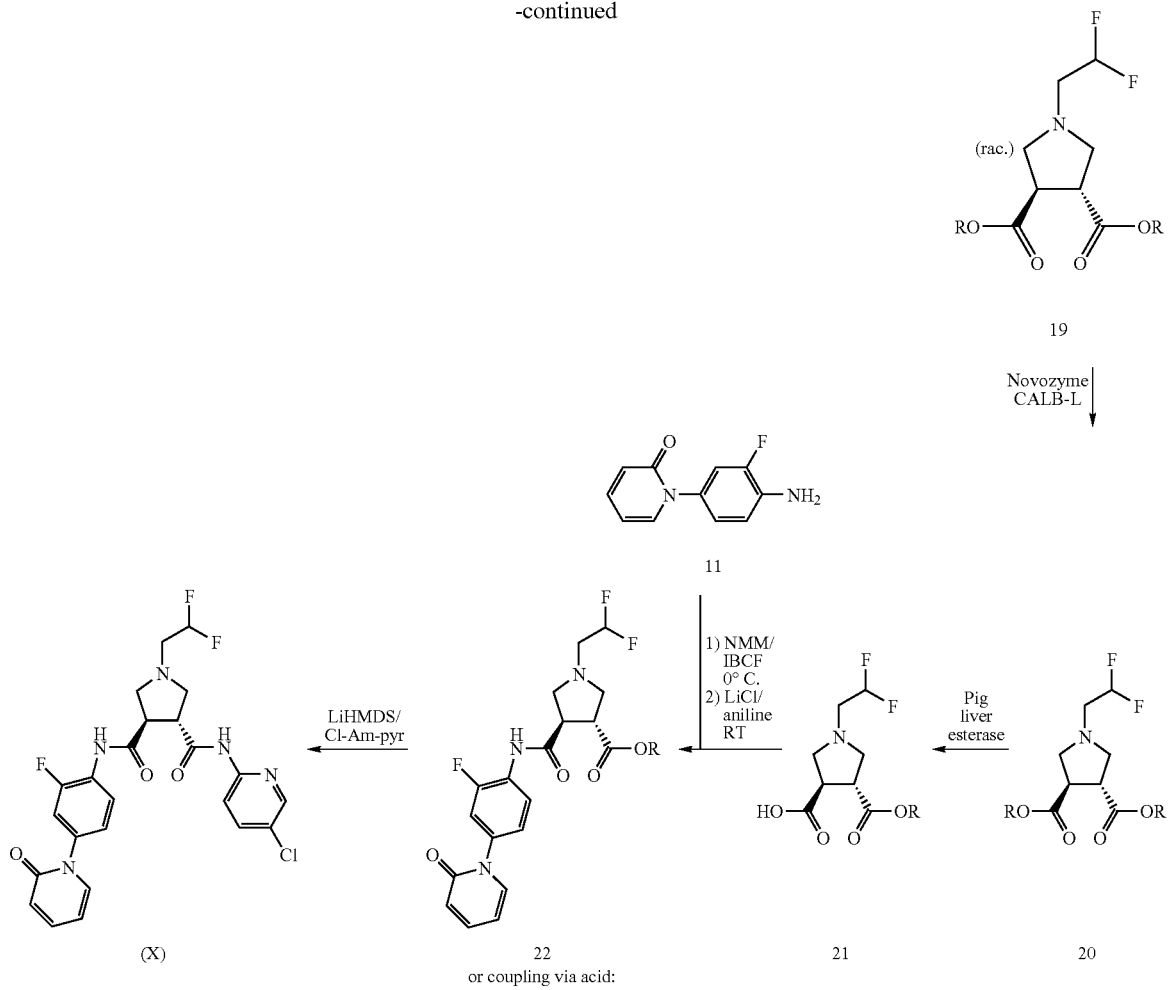

In scheme 5, R is $C_{1-5}$ alkyl or $C_{1-3}$ alkyl substituted by one or more substituents selected from the group consisting of hydroxyl, methoxy, ethoxy and halogen. R is preferably $C_{1-3}$ alkyl optionally substituted by halogen, methoxy or hydroxy, more preferably $C_{1-3}$ alkyl, especially methyl.

Compound (X) is also accessible through the enzymatic resolution of N-(2,2-difluoroethyl)-pyrrolidine-3,4-dicarboxylic acid diester as outlined in the previous scheme. The route can be carried out in the ester series as defined above, but is preferably performed in the methyl ester series.

The racemic esters are prepared via a [3+2] cycloaddition between the appropriate fumarate diester and the azomethine ylide derived from the combination of amine 1 and formaldehyde under conditions already describe vide supra. The resulting N-benzyl-pyrrolidine dicarboxylic acid diester is deprotected under conditions known by the person skilled in the art. The pyrrolidine is then alkylated under conditions described earlier for analogous substrates (i.e. by reaction with difluoroethyl triflate or difluoroethyl 3-nitrobenzenesulfonate, in an appropriate solvent or solvent mixture and in the presence of an appropriate base). The racemic diester is then resolved leading to the desired (R,R)-pyrrolidine diester. The latter is then monohydrolyzed to the monoacid monoester which in turn is transformed to compound (X) under conditions described in this patent for analogous substrates.

The sequence comprises:

1. A [3+2] cycloaddition between fumaric acid diester and the azomethine ylide derived from a combination of amine 1 and formaldehyde to provide pyrrolidine 17
2. A debenzylation of 17 to provide 18.
3. The alkylation of pyrrolidine 18 providing compound 19
4. The resolution of the (rac)-pyrrolidine diester 19 to the (R,R)-pyrrolidine diester 20
5. The monohydrolysis of pyrrolidine diester 20 to the (R,R)-mono acid monoester 21.
6. The coupling of mono acid monoester 21 with aniline 11 to give mono amide monoester
7. The direct coupling of monoester mono amide 22 with 2-amino-5-chloropyridine.

Alternatively, pyrrolidine 19 can be directly accessed by the steps comprising:

1. Alkylating trimethylsilylmethyl amine with an alkylating agent, such as 2,2-difluoroethyl triflate, 2,2-difluoroethyl tosylate, 2,2-difluoroethyl n-nitrobenzenesulfonate (n=2,3,4), 2,2-difluoroethyl 2,4-dichlorobenzenesulfonate and 2,2-difluoroethyl mesylate, preferably 2,2-difluoroethyl triflate or 2,2-difluoroethyl 3-nitrobenzenesulfonate, more preferably 2,2-difluoroethyl triflate, leading to N,N-(trimethylsilylmethyl)-(difluoroethyl)-amine 29.

2. In turn, reagent 29 is reacted with formaldehyde, fumaric acid diester in the presence of an acid (in sufficient amount as to at least protonate any excess of base used in the alkylating step), leading to the corresponding [3+2] cycloaddition product, i.e. pyrrolidine 19.

Alternatively, amide ester 22 can be converted to 10 via ester hydrolysis to the corresponding amide acid and coupling of the acid function with 2-amino-5-chloropyridine under condition known by the person skilled in the art.

Enzymatic Resolution/Monohydrolysis

Scheme 7

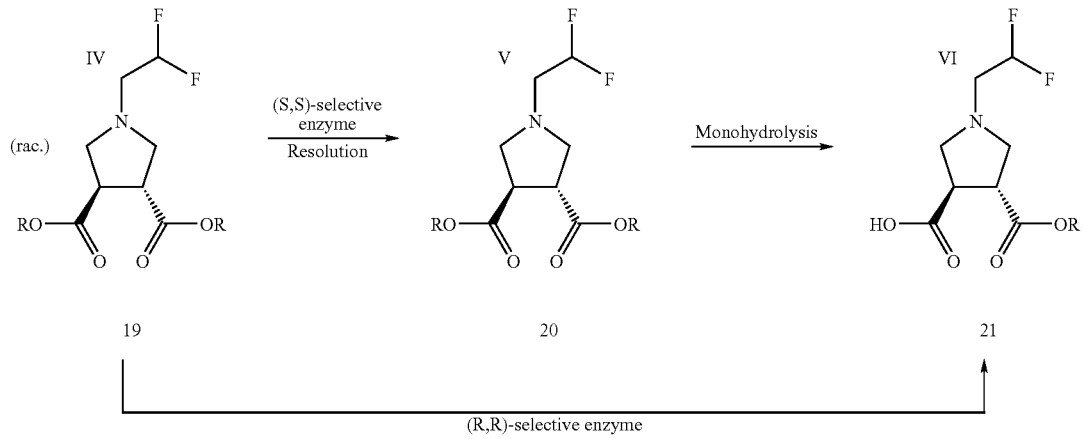

Alternatively, the cycloaddition step can be performed under thermal conditions.

Scheme 6

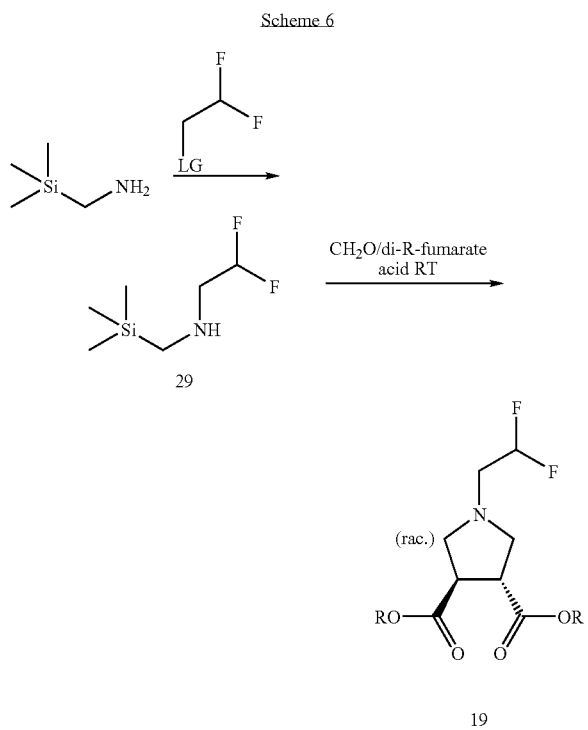

In scheme 6, R is $C_{1-5}$ alkyl or $C_{1-3}$ alkyl substituted by one or more substituents selected from the group consisting of hydroxyl, methoxy, ethoxy and halogen. R is preferably $C_{1-3}$ alkyl optionally substituted by halogen, methoxy or hydroxy, more preferably $C_{1-3}$ alkyl, especially methyl.

In scheme 7, R is $C_{1-5}$ alkyl or $C_{1-3}$ alkyl substituted by one or more substituents selected from the group consisting of hydroxyl, methoxy, ethoxy and halogen. R is preferably $C_{1-3}$ alkyl optionally substituted by halogen, methoxy or hydroxy, more preferably $C_{1-3}$ alkyl, especially methyl. (R,R)—N-(2, 2-difluoroethyl)-pyrrolidine-3,4-dicarboxylic acid monoesters of formula 21 are used as intermediates to prepare compound of formula (X). Preferred $C_{1-3}$ alkyl for R is methyl or ethyl. In formula 19, 20 and 21, preferentially R is ethyl or methyl, most preferred is methyl.

The intermediates 21 can be prepared through chemoenzymatic procedures based on kinetic racemic resolution described below.

1. Enantioselective enzymatic hydrolysis of trans-racemic N-(2,2-difluoroethyl-pyrrolidine-3,4-dicarboxylic acid diester 19 as outlined in Scheme 7 and 2. selective monohydrolysis of the retained (R,R)—N-(2,2-difluoroethyl)-pyrrolidine-3,4-dicarboxylic acid diester 20 in an aqueous buffer according to Scheme 7.

The enantioselective hydrolysis (Scheme 7) is carried out by contacting an enzyme with the diester substrate 19 emulsified in an aqueous buffer by vigorous stirring until the retained diester 20 has reached a high enantiomeric excess (>50% conversion).

Several enantioselective enzymes could be found when applying appropriate reaction conditions: Lipase from *Candida antarctica* form B, lipase from *Phycomyces nitens*, protease from *Bacillus* sp. (Esperase 4.0 T; Novozymes), subtilisin from *Bacillus* sp. (Alcalase 2.5L; Novozymes) and esterase ESP-ESL-1199. Preferred are lipase from *Candida antarctica* form B, lipase from *Phycomyces nitens* (Lipase P N, Wako Pure Chemical Industries, Ltd.; Osaka, Japan) and esterase ESP-ESL-1199 (Diverasa Corporation; San Diego, USA), and most preferred is lipase from *Candida antarctica*, form B (commercial preparations of which are Lipozyme CALB L or Novozyme CALB L; Novozymes; Bagsvaerd, Denmark).

Suitable buffers are the conventional buffers commonly used in biochemistry in the range of pH 5-9, preferably 6-8. In the course of the reaction, the pH of the reaction mixture is kept constant at the selected value by the addition of a base, preferentially NaOH or KOH-solution.

In the case of esterase ESP-ESL-1199, the use of phosphate buffer (e.g. 30 mM) of pH7.2 with additives, such as magnesium acetate (e.g. saturated), acetonitrile (e.g. 5% v/v) and ethanol (e.g. 5% v/v) is benificial for selectivity (E>>40). Also a pH below 7 (e.g. MES-buffer pH6.2) enhances selectivity.

In the case of lipase from *Candida antarctica* form B, the use of phosphate buffer (e.g. 30 mM) of pH7.2 with additives, such as potassium sulfate (e.g. 0.5M), potassium chloride (e.g. 0.5M), lithium rhodanide (e.g. 0.1M), magnesium acetate (e.g. saturated), polyethyleneglycol 6000 (e.g. 10% w/v), guanidinium chloride (e.g. 0.1M), D-glucose (e.g. 0.5M), DMSO (e.g. 5% v/v) and ethanol (e.g. 5% v/v) is benificial for selectivity (E>>40). Also a pH below 7 (e.g. acetate or MES-buffer) enhances selectivity.

All enzymes might be applied at a lower temperature (0-25° C.) in order to enhance the enantioselectivity. The activity of the enzyme can be increased by working at higher temperature however at the cost of selectivity. As an alternative, the enzymes may be used in immobilized form.

After termination of the reaction, the diester product is worked up conventionally by extraction.

The retained, enantiomerically pure (R,R)-diester 20 is then monohydrolyzed to enantiomerically pure (R,R)-monoester 21 by contacting it in an aqueous system with lipases, esterases, cholestrases or proteases. Pig liver esterase—a commercial preparation of which e.g. is PLE Technical Grade from Roche Applied Sciences (3.12 MU/L; Catalogue No. 10491228; Penzberg, Germany)—and Lipase OF from *Candida cylindracea* (*C. rugosa*; Meito Sangyo; Tokyo, Japan) turned out as the most suitable enzymes.

The substrate concentration may range from 1-20% w/w, preferably from 5-15% w/w.

The monoester product is extracted from the aqueous phase by repeated extraction with ethyl acetate at pH 3.5-4 (with adjustment of the pH between the extraction steps, or use of a strong pH 3.5-4 phosphate buffer).

Optionally, the (R,R)-monoester 21 might be synthesized directly from diester 19 by enantioselective monohydrolysis using a highly (R,R)-selective enzyme.

V Cyclic Anhydride Route

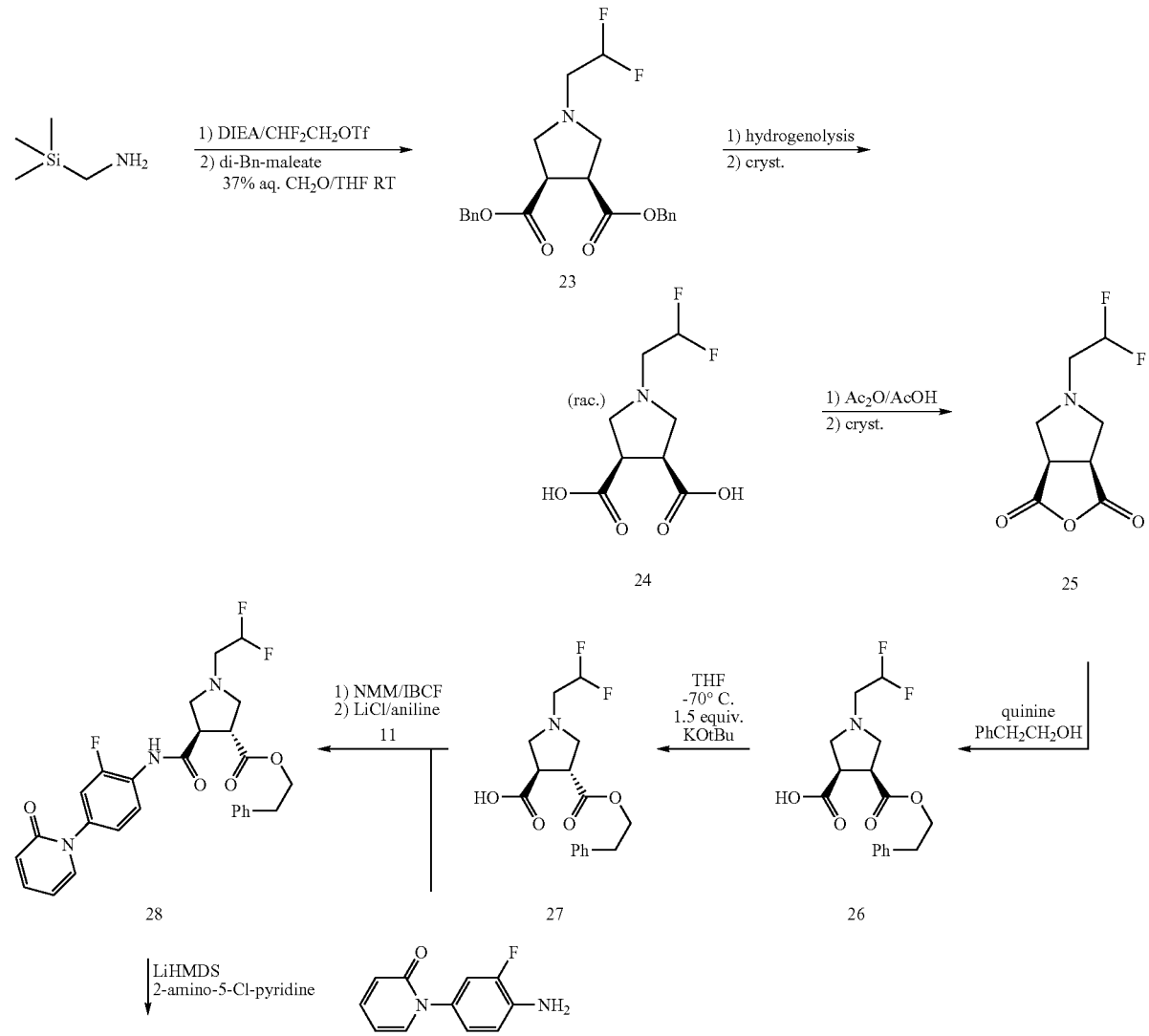

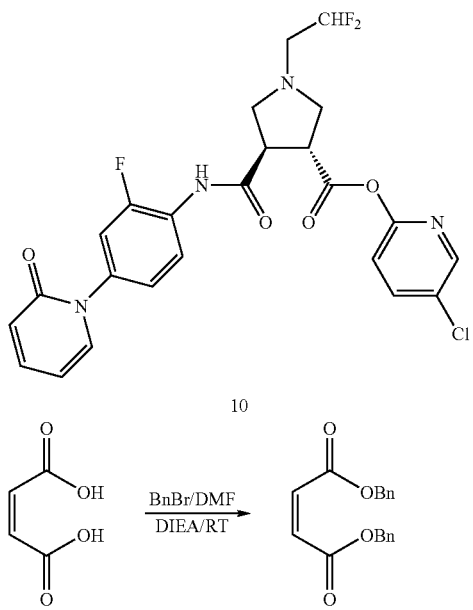

In scheme 8, $R^1$ is methyl, ethyl, cinnamyl, benzyl or phenethyl.

This route comprises the following steps:
1. A [3+2] cycloaddition reaction leading to the difluoroethyl pyrrolidine 23
2. The benzyl ester hydrogenolysis providing the cis bis-acid 24
3. The formation of the cyclic anhydride 25
4. Anhydride desymmetrization to form the cis mono acid mono ester 26
5. The epimerization of the alpha ester center to the corresponding trans mono acid mono ester 27
6. The first amide coupling with aniline 11 giving the amide ester 28
7. The direct coupling of ester amide 28 with 2-amino-5-chloropyridine leading to compound 10

The conditions for the cycloaddition step (formation of 23) are similar to those described for the preparation of pyrrolidine 19 from (trimethylsilyl-methyl)-amine via reagent 29.

Hydrogenolysis of 23 to 24 is performed under conditions known by the person skilled in the art. Depending on the condition used, crystallization can occur during the hydrogenolysis. This can be avoided by performing the hydrogenolysis in the presence of tertiary amines, such as triethylamine and diisopropylethyl amine, preferably in the presence of triethylamine. The bis acid 24 is best crystallized from acetic acid or a mixture of acetic acid and a solvent, such as toluene, ethyl acetate, isopropyl acetate and MTBE, preferably in a mixture of acetic acid and MTBE. It has to be noted that the epimerization to the corresponding trans acid can occur for example when the cis acid 24 is heated in acetic acid. The work-up conditions have to be carefully chosen to avoid this epimerization. It is however possible to convert the trans isomer of 24 to the cyclic anhydride, although under more drastic conditions (see vide infra).

The formation of the cyclic anhydride is performed by reacting the cis bis acid 24 with a dehydrating agent, such as a sulfonyl chloride, a phosphorous oxide ($OPCl_3$, $P_2O_5$), a phosphorous halide ($PCl_3$, $PCl_5$, $PBr_3$) or a carboxylic acid anhydride, such as propionic anhydride and acetic anhydride. Preferred conditions involve the use of acetic anhydride in a suitable solvent, preferably acetic acid.

Compound of formula 26 is accessed via the desymmetrization reaction of a meso cyclic anhydride (see for examples Bolm et al, *Tetrahedron: Asymmetry* 2003, 3455; Bolm et al, *J. Org. Chem.* 2000, 6984; Deng et al patent US 2004/0082809; Deng et al, *J. Am. Chem. Soc.* 2000, 9542) of formula 25.

The cyclic anhydride desymmetrization by selective opening with an alcohol is performed in the presence of a chiral reagent, such as a chiral amine, especially cinchona alkaloids or derivatives thereof, preferably in the presence of quinine. The reaction can be performed in an organic solvent, such as THF, toluene, ethyl acetate, isopropyl acetate, acetone, MTBE, 2-methyl-THF and acetonitrile, preferably in THF, toluene or 2-methyl-THF, more preferably in toluene or THF (see following table).

Results from a screening performed with quinine as promoter and BnOH as nucleophile:

| e.r. | −15° C. 1 equiv. quinine | 25° C. 1 equiv. quinine | −15° C. 0.2 equiv. quinine | −15° C. 1 equiv. EtiPr$_2$N 0.2 equiv. quinine |
|---|---|---|---|---|
| DMSO | 75:25 | 55:45 | | |
| Toluene | 93:7 | 88:12 | 82:18 | 86:14 |
| Acetone | 86:14 | 80:20 | | |
| DMF | | 58:42 | | |
| MTBE | 92:8 | 86:14 | 88:12 | 85:15 |
| THF | 92:8 | 86:14 | 85:15 | 84:16 |
| MeCN | 77:23 | 70:30 | | |
| AcOEt | 88:12 | 77:23 | | |
| iPrOAc | 92:8 | | 87:13 | 84:16 |
| 2-Me-THF | 93:7 | | 90:10 | 87:13 |
| CF$_3$-Ph | | | 80:20 | 81:19 |

Mixture of solvents are also possible. However, the optimal balance between reagents solubility, reactivity and selectivity has to be found.

The reaction can be performed with substoichiometric amounts of quinine. However, in this case, the reaction is best performed in the presence of an additive, preferably a non-nucleophilic base, such as Hünig's base and tetramethylpiperidine, preferably in the presence of Hünig's base. The reaction is performed at a temperature chosen between −80° C. and 50° C., preferably between −40° C. and 25° C., more preferably around −20° C.

When quinine is used as promoter, the anhydride can be opened with alcohol, such as methanol, ethanol, propanol, butanol, benzyl alcohol, cinamyl alcohol and 2-phenyl-ethanol, preferably with methanol, ethanol, benzyl alcohol, cinamyl alcohol or 2-phenyl-ethanol, more preferably with ethanol, benzyl alcohol or 2-phenyl-ethanol, more preferably with 2-phenyl-ethanol. Under optimal conditions, the products are obtained in 90-95: 10-5 enantiomeric ratio.

The product can be isolated by work-up known by the person skilled in the art, such as by extraction. In some cases, their quinine salt can be directly isolated from the reaction mixture or after an appropriate solvent exchange.

The enantiomeric purity of the mono acid mono ester can be, in some instance, upgraded by the crystallization/re-crystallization of their salt with an amine for example quinine. The enantiomeric purity can be upgraded by crystallization of the acid from water as in the case of mono acid mono ester 26, wherein R is $PhCH_2CH_2$.

The epimerization of the cis mono acid monoester 26 to the corresponding trans mono acid mono ester 27 is performed under basic conditions, using >1 equivalent, preferably 1.05-3 equivalents, more preferably 1.1-2 equivalents, more preferably 1.3-1.6 equivalents of a strong base, such as LiHMDS, KHMDS, NaHMDS, LDA, KOtBu, NaOtBu, LiOtBu, lithium t-amylate, potassium t-amylate and sodium t-amylate. A preferred base is KOtBu or potassium t-amylate, especially KOtBu. The reaction is performed in a solvent such as toluene, THF, DME and dioxane, preferably in toluene or THF, more preferably in THF. The reaction is performed at a temperature chosen between −80° C. to 50° C., preferably between −80° C. and room temperature, more preferably between −80° C. and −15° C., even more preferably between −80° C. and −60° C.

Care must be taken that the starting mono acid mono ester 26 is fully dissolved or at least exhibits sufficient solubility as to allow its reaction with the base. In the case of unfavorable solubility, the addition of a tertiary amine forming a soluble salt may solve the problem. Preferred amine are for example triethylamine tributylamine or diisopropylethylamine, more preferably triethylamine.

The diastereomeric purity (trans:cis) is generally around 99% in the crude mixture. In the case wherein R is $PhCH_2CH_2$, this can be further increased after work-up and crystallization from water.

In the case wherein R is $PhCH_2CH_2$, both the enantiopurity and diastereomeric purity can be upgraded by (re)-crystallization in, for example, a mixture of ethyl acetate and heptane. The conversion of 27 to 10 is performed under conditions already described in the present patent for analogous substrates.

The cyclic anhydride 25 can also be accessed via the sequence depicted in the following scheme and comprises the following steps:
1. Cycloaddition between trimethylsilylmethyl amine/formaldehyde/dibenzyl fumarate under conditions similar to the conditions already described for the transformation of 12 to 13, leading to the aminal 30 (mixture of isomers, all trans relative configuration between neighboring ester groups, wherein R is benzyl).
2. The in-situ cleavage of the aminal to the corresponding amine, which is isolated as the hydrochloride 31.
3. Alkylation of the corresponding free amine of 31 leading to 32 under conditions already described in this patent for analogous substrates.
4. Benzyl ester hydrogenolysis leading to the trans bis acid 33
5. Anhydride formation.

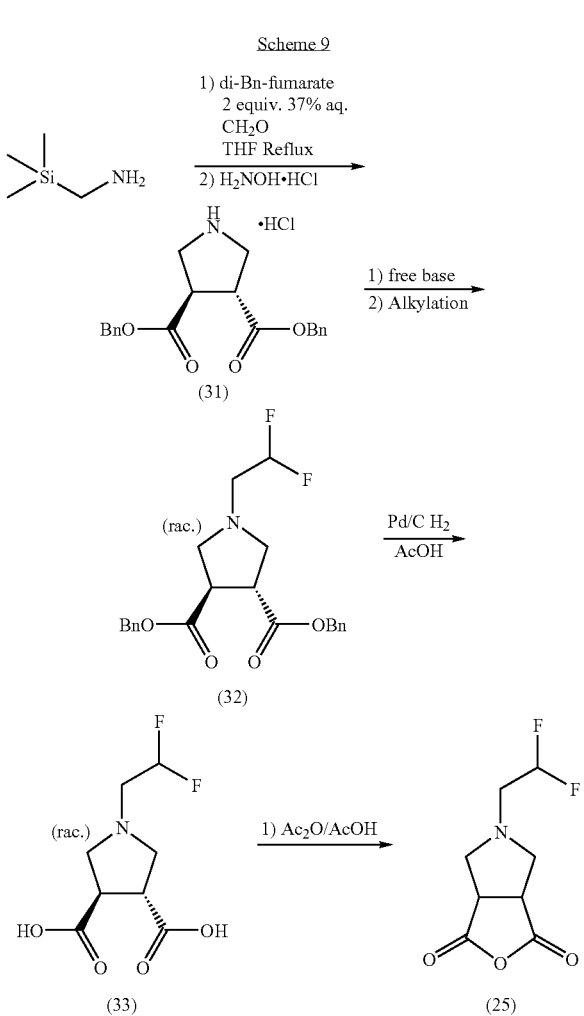

Scheme 9

The trans bis acid 33 can be converted directly to the cis-anhydride 25. Indeed under suitable reaction conditions, equilibrium between the cis and trans isomers of 33 exists. The cis isomer is then trapped by acetic anhydride and converted to the desired anhydride. Reactions conditions are similar to the conditions used for the conversion of 24 to 25 with the exception that the reaction temperature has to be increased in order to allow fast enough trans-cis isomerization. Preferred conditions comprise the reaction of bis acid 33 with acetic acid anhydride at a temperature between 60° C. and 140° C., preferably between 80° C. and 120° C., more preferably between 100° C. and 110° C., in a suitable solvent, preferably acetic acid.

Bis acid 33 can also be obtained by hydrolysis of the corresponding esters (for example dimethyl-, diethyl-, dibenzyl-, dipropyl, diisopropyl-, dibutyl-esters) and crystallization from water at pH 3-3.5.

Preparation of 1-(4-amino-3-fluoro-phenyl)-1H-pyridin-2-one (compound 11)

The process described in patent US2005/0215599, i.e. copper catalyzed N-arylation of 2-hydroxypyridine with 4-bromo-2-fluoroaniline suffers from a major safety issue.

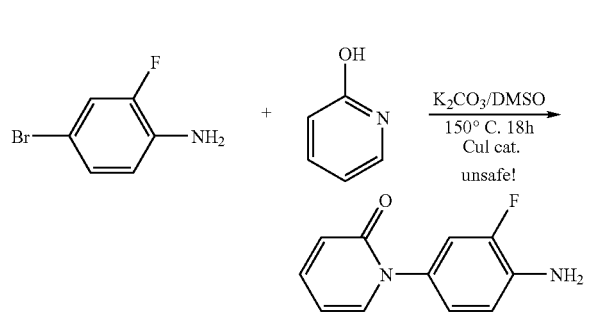

Indeed mixture of K₂CO₃ and DMSO at high temperature are potentially leading to a runaway event which would be accompanied by a very high adiabatic temperature increase. The time to maximum rate for the runaway event (from ARC measurements) is in the order of the reaction time, hence such a process cannot be scaled up as it stands.

A first modification of the process involved the replacement of DMSO by NMP or DMA preferably DMA.

The copper (I) source can be CuI, CuCl, CuBr, Cu₂O, preferably CuI and Cu₂O, more preferably Cu₂O.

Preferred conditions for the N-arylation comprise the use of 0.05 to 1 equiv. of Cu₂O, preferably 0.05-0.5 equiv., more preferably 0.1-0.2 equiv., in DMA, in the presence of K₂CO₃, at a temperature between 110° C. and 150° C., more preferably between 120-140° C., even more preferably between 130-140° C.

Other preferred conditions comprises the use of pyridine as solvent and 0.1 to 1 equiv. of Cu₂O, more preferably 0.25 to 0.75 equiv., even more preferably around 0.5 equiv., at a temperature between 100-150° C., preferably between 100-120° C. (for temperature over the boiling point, an autoclave is used).

In both cases, the product is isolated via crystallization, by addition of water.

If necessary, the product can be further purified by a charcoal treatment and/or recrystallization in ethanol or methanol, preferably methanol.

The N-arylation can also be performed in toluene in the presence of a ligand like trans-cyclohexyl-1,2-diamine, TMEDA, ethylenediamine, trans-N,N'-dimethyl-cyclohexyl-1,2-diamine, N,N'-dimethylethylene-1,2-diamine, preferably trans-N,N'-dimethyl-cyclohexyl-1,2-diamine and TMEDA, preferably TMEDA.

The aniline 11 can also be prepared by a sequence involving first the protection of the 4-bromo-2-fluoroaniline, followed by the N-arylation (under conditions similar to the one described here above on the unprotected aniline), followed by the deprotection. 4-bromo-2-fluoroaniline is preferably protected by a bis-benzylation. Crystalline intermediates are obtained in each steps. The deprotection step requires careful monitoring of the hydrogenolysis in order to avoid hydrogenation of the pyridone ring. Proper choice of the catalyst is also crucial, in our hand 5% Pd/C from Johnson Matthey gave the best results.

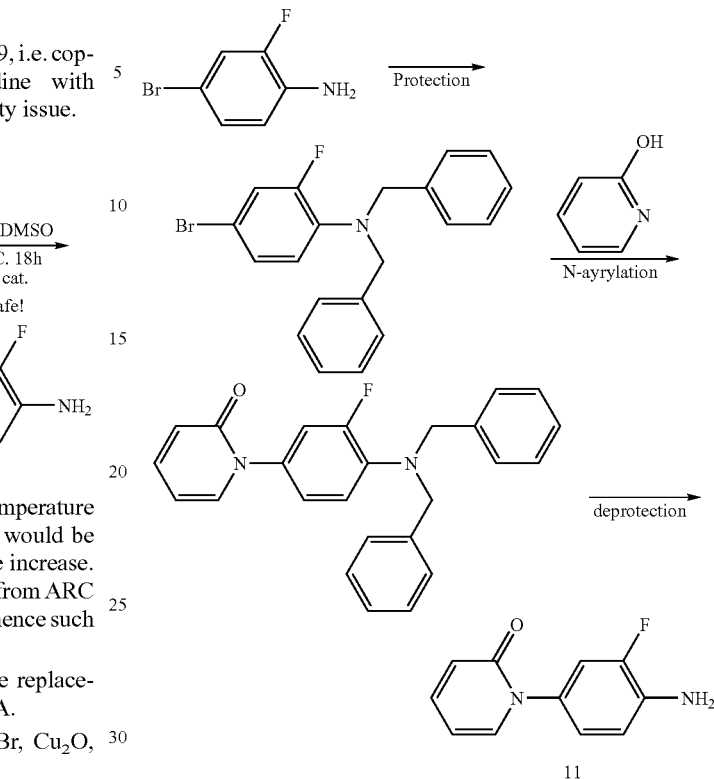

EXAMPLES

The following Examples serve to illustrate the present invention in more detail. They are, however, not intended to limit its scope in any manner.

Example 1

Enzymatic route A

Step 1: [3+2] Cycloaddition

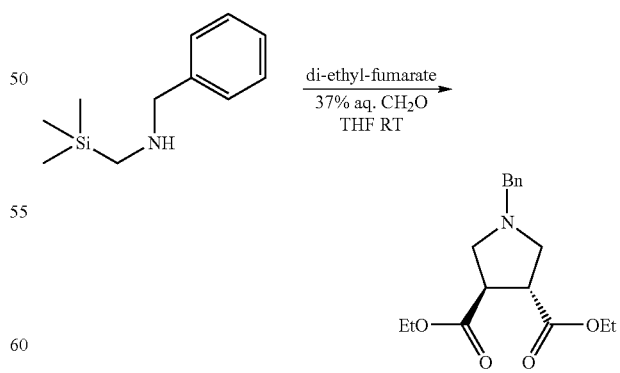

900 g of N-Benzyl-N-trimethylsilylmethyl-amine (4654 mmol) were dissolved in 5.6 l THF at 20-25° C. 450 ml of 36% aqueous formaldehyde (5880 mmol, 1.26 equiv.) were added over 15 min, keeping the temperature between 20-25° C. After 15 min, a mixture of 760 ml diethyl fumarate (1 equiv.), 2.25 l THF and 11.2 ml trifluoroacetic acid (0.03 equiv.) was added over 15 min. The reaction mixture was stirred overnight keeping the temperature between 20-30° C. (in process control by GC). 3.5 l of 1N HCl were added, followed by 2.3 l heptane. The aqueous phase was separated and washed with 3.4 l heptane. The heptane phases were washed sequentially with 3.5 l 1N HCl. 4.5 l MTBE were added to the combined aqueous phases. 720 ml of 32% NaOH$_{aq}$ were added (pH 13) under vigorous stirring. The aqueous phase was separated and re-extracted with 4.5 l MTBE. The MTBE phases were washed sequentially with 2.2 l water, combined and concentrated to dryness at 45° C. to give 1.295 kg of crude (rac)-trans-N-benzyl-pyrrolidine-3,4-dicarboxylic acid diethyl ester. If required, the crude cycloadduct can be distilled.

Step 1: [3+2] Cycloaddition (Alternative Conditions)

200 g of N-Benzyl-N-trimethylsilylmethyl-amine (1035 mmol) were dissolved in 800 ml THF. To this solution, at room temperature, were added 98.3 ml 37% aqueous formaldehyde solution (1.26 equiv.). After 15 min stirring at room temperature, the resulting solution was added over 2 h to a hot (50-55° C.) solution consisting of 181.8 g diethyl fumarate (1035 mmol), 1.2 l THF and 2.5 ml trifluoro acetic acid (0.03 equiv.). After completion of the reaction (IPC by GC or HPLC), the reaction mixture was cooled to room temperature and worked up as described in the previous example to provide 301.8 g of the expected cycloadduct.

Step 2-3: De-benzylation/Boc Protection

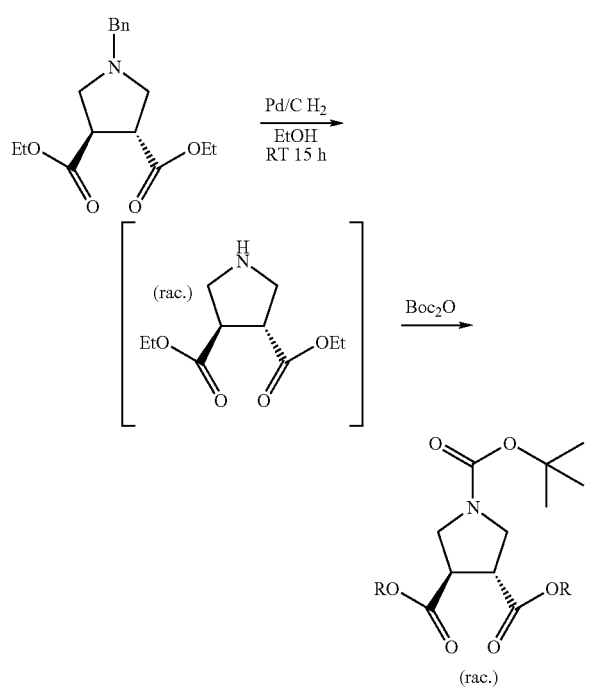

1.295 kg (rac)-trans-1-Benzyl-pyrrolidine-3,4-dicarboxylic acid diethyl ester were hydrogenated at room temperature, in 6.5 l EtOH with 100 g 10% Pd/C catalyst. After completion of the reaction, the catalyst was filtered and a solution of 935 g di-t-butyl-dicarbonate (1.01 equiv) in 480 ml EtOH was added. After completion of the reaction (in process control by GC), the reaction mixture was evaporated, dissolved in 9.7 l THF. 8 ml water were added, followed by 5.3 g DMAP (0.01 equiv.). The reaction mixture was stirred 30 min. at room temperature and concentrated to dryness. The residue was dissolved in 6.5 l MTBE, washed with 1.29 l 5% aqueous citric acid solution, 3.3 l 10% aqueous NaHCO$_3$ solution and 3.3 l water. The aqueous phases were re-extracted sequentially with 6.5 l MTBE. The combined organic phases were dried over Na$_2$SO$_4$ and concentrated to dryness at 40° C. to give 1.233 kg of crude (rac)-trans-N-Boc-pyrrolidine-3,4-dicarboxylic acid diethyl ester.

Rem.: the DMAP quench may be omitted when performing the enzymatic resolution with the Lipolase 100L type EX enzyme.

Step 4: Enzymatic Resolution (Lipolase)

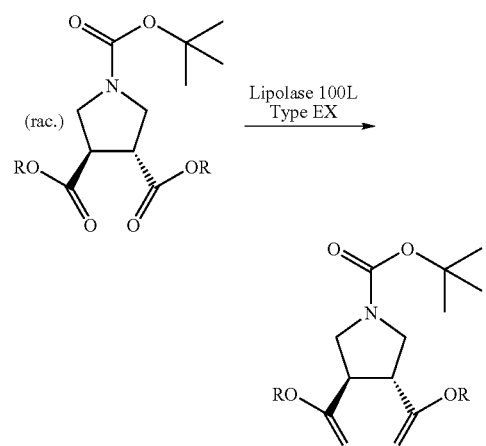

32 g (rac)-trans-N-Boc-pyrrolidine-3,4-dicarboxylic acid diethyl ester (96.19 mmol, 95a % GC) was emulsified under vigorous stirring in 32 ml heptane and 256 ml 0.1 M sodium phosphate buffer pH 7.0. The emulsion was cooled to 0-1° C. 2.30 ml Novozyme Lipolase 100L Type EX (Novozyme) was added and the pH kept constant at 7.0 by the automated addition (pH-stat) of 1.0 M NaOH-solution. After reaching the targeted enantiomeric excess, (typically >99%, ca 45 h reaction time, 0.55 equiv. NaOH added, GC in process control), 250 ml dichloromethane was added. The aqueous phase was separated and extracted twice with 500 ml dichloromethane. The combined organic phases were evaporated during which a white precipitate was formed. The residue was re-dissolved in 250 ml ethyl acetate and the white precipitate was filtered off. The filtrate was washed with 75 ml saturated aqueous sodium bicarbonate solution. The organic phase was dried over sodium sulfate, evaporated and dried under high vacuum overnight to give 13.47 g, (3R,4R)-trans-N-Boc-pyrrolidine-3,4-dicarboxylic acid diethyl ester as a light yellow oil (96% pure by GC).

The product can alternatively be extracted with heptane or MTBE, preferably heptane. NaCl can also be added to the aqueous phase to facilitate the phase separations.

Step 5: Selective Monohydrolysis

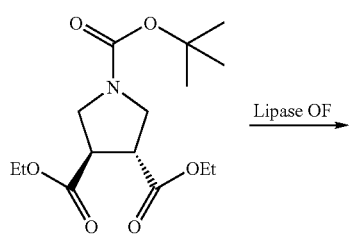

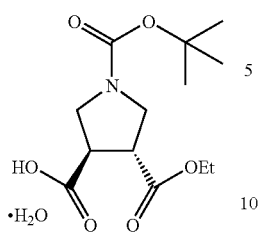

2.95 kg (3R,4R)-trans-N-Boc-pyrrolidine-3,4-dicarboxylic acid diethyl ester were stirred in 26.5 l of an aqueous 5 mM potassium phosphate/1 M D-glucose buffer to form an emulsion. 5.9 g of Lipase OF (Meito Sangyo) dissolved in 0.5 l water was added. The pH was kept at 7.2 by addition of 1M NaOH. After completion of the reaction (8.4 kg 1M NaOH, 24 h reaction time, GC in process control), 10 l MTBE were added. The organic layer was separated and discarded. 40 l ethyl acetate were added and the pH was adjusted to 4 by addition of $H_2SO_4$. The organic layer was separated and the aqueous phase was re-extracted with 40 l ethyl acetate. The combined organic phases were evaporated to dryness to give 2.35 kg of (3R,4R)-trans-N-Boc-pyrrolidine-3,4-dicarboxylic acid monoethyl ester.

The (3R,4R)-trans-N-Boc-pyrrolidine-3,4-Dicarboxylic Acid Monoethyl Ester Can Be Crystallized in Acetone/Water:

3.2 kg of (3R,4R)-trans-N-Boc-pyrrolidine-3,4-dicarboxylic acid monoethyl ester were dissolved in 3.2 l acetone. To this solution, 3.2 l of 0.1% aqueous acetic acid solution were added at room temperature. The turbid solution was seeded. The crystallization started after 15 min. After an additional 30 min, 30 l water were added and the suspension was stirred 22 h at room temperature. The suspension was filtered. The filter cake was washed in portions with water, in total 7 l and was dried to constant weight to give 3.295 kg of (3R,4R)-trans-N-Boc-pyrrolidine-3,4-dicarboxylic acid monoethyl ester monohydrate as a white powder.

Step 6: First Amide Coupling

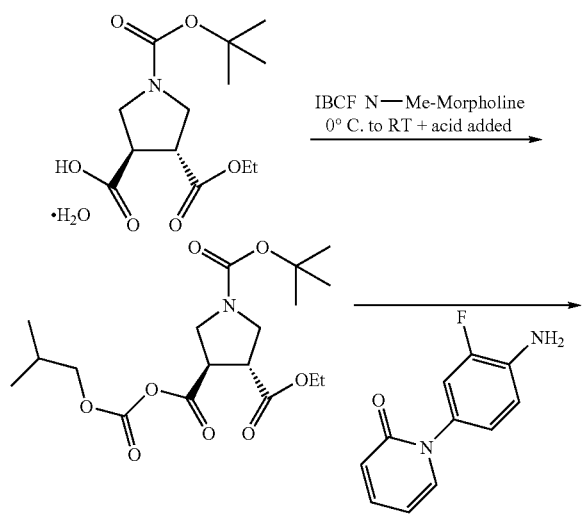

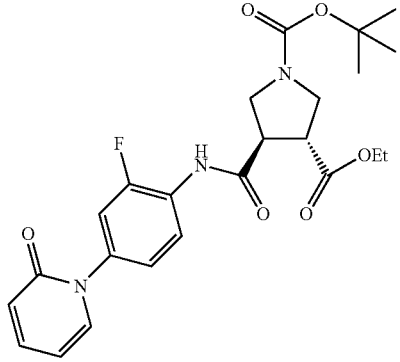

135 g trans-N-Boc-pyrrolidine-3,4-dicarboxylic acid monoethyl ester monohydrate were suspended in 700 ml toluene and concentrated to 150-200 ml (60° C. jacket temperature under ca 100 mbar; azeotropic removal of water, residual water content checked by Karl Fischer analysis). 400 ml THF were added followed by 55 ml N-methylmorpholine (1.11 equiv). The resulting solution was added over 30 min to a cold (0-5° C.) solution of 60 ml (1.04 equiv.) isobutyl chloroformate in 900 ml THF. The addition funnel was washed with 50 ml THF. The white suspension was stirred 15 min at 0-5° C. 90 g of the fluoroaniline (1.0 equiv.) were added in one portion and the reaction mixture was heated at reflux. After completion of the reaction (HPLC in process control), the reaction mixture was cooled to RT. 900 ml toluene were added followed by 500 ml 1M HCl. The aqueous phase was separated and extracted with 900 ml toluene. The organic phases were washed sequentially with 500 ml HCl 1 M and 500 ml 5% aqueous $NaHCO_3$ solution. The organic phases were combined, dried over $Na_2SO_4$ and concentrated to ca 500 ml (60° C. jacket temperature). The isobutanol was removed by azeotropic distillation at constant volume with ca 1 l toluene (isobutanol removal checked by GC). The crude product solution was then concentrated to 337 g (60% m/m solution in toluene which was used directly in the next step, corresponds to 97% yield).

Alternatively, the reaction can be performed at room temperature with LiCl activation: 10 g of mono acid monoester as monohydrate (32.75 mmol 1 equiv.) was dissolved in 100 ml THF, dried over $MgSO_4$, filtered, concentrated to dryness and re-dissolved in 30 ml THF together with 4.15 ml N-methyl-morpholine (1.15 equiv.). This solution was added over 15 min., to a cold 0-5° C. solution of 4.46 ml of isobutlychloroformate (1.0 equiv.) in 50 ml THF. After 1.5 h at 0-5° C. (the hold time can be shorter since the activation step is mainly feed controlled. This would also reduce any mixed anhydride decomposition), 1.4 g of lithium chloride (1.0 equiv.) were added followed by 6.88 g of aniline (adding the aniline first, followed by the LiCl is also possible). After 18 h reaction at room temperature, 150 ml toluene were added. The reaction mixture was washed twice with 60 ml HCl 1N, 60 ml 5% $NaHCO_3$ $_{aq}$ and 60 ml half saturated aqueous NaCl solution. The aqueous phases were re-extracted sequentially with 100 ml toluene. The organic phases were combined, dried over $MgSO_4$, filtered and concentrated to dryness under reduced pressure at 45° C. to give 15.92 g of a foam (ca 97% yield, contains ca 4% toluene). Isobutanol removal has to be ensured. Additional azeotropic removal is possible see previous example.

Step 7: Second Amide Coupling

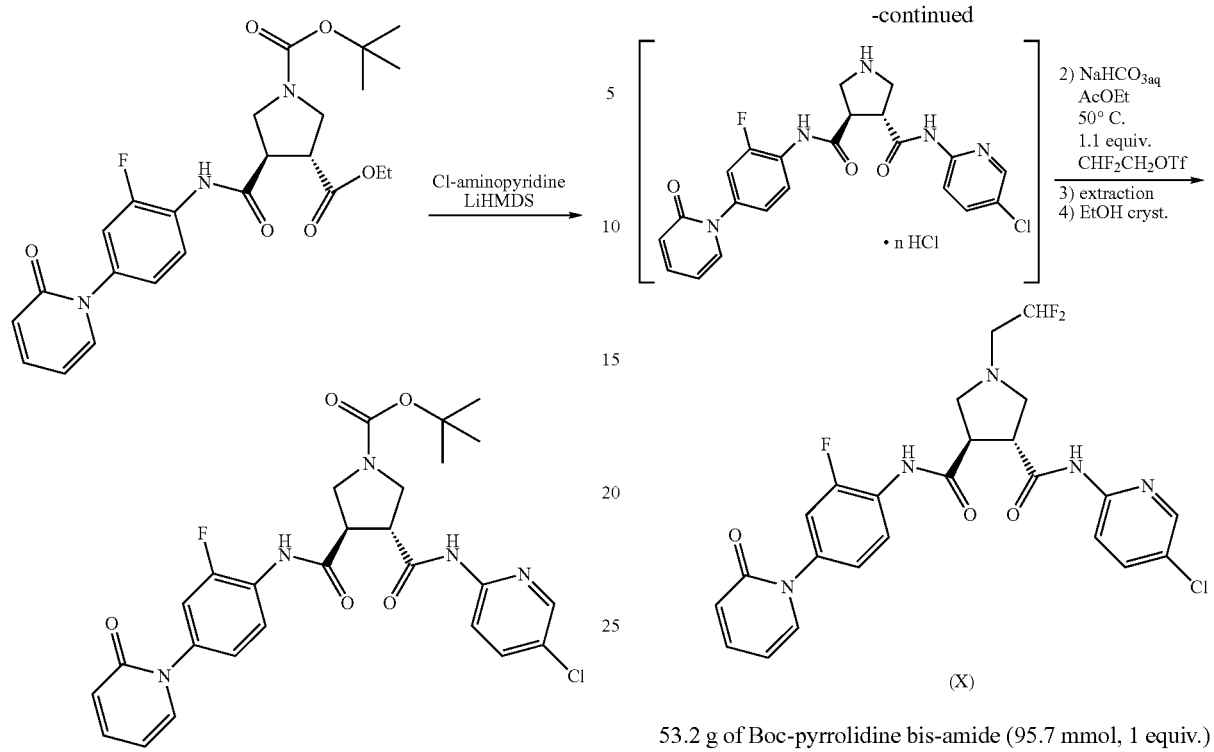

337 g of a 60% m/m of the amide ester (see previous step) solution in toluene (431 mmol, 1 equiv.) was charged in the reactor, followed by 650 ml THF. 86 g 5-chloro-2-aminopyridine (1.5 equiv.) were added. 1.2 l of 1M LiHMDS solution in THF was added over 30 min. keeping the temperature between 20-25° C. After completion of the reaction (HPLC in process control), a solution consisting of 300 ml 37% $HCl_{aq}$ in 1.2 l water was added (pH 1-2). 2 l dichloromethane were added and the organic phase was separated and washed with 1 l water. The aqueous phases were extracted sequentially with 1 l dichloromethane. The combined dichloromethane phases were concentrated to a volume of 2.5-3.5 l. A solvent exchange to ethanol was performed at constant volume (60° C. jacket temperature, 400 to 100 mbar, 5 l ethanol in total) during which crystallization started. The suspension was cooled to RT, stirred overnight at RT and 2 h at 0-5° C. The suspension was filtered and the filter cake was washed 4 times with 250 ml cold (−20° C.) EtOH. The crystals were dried at 45° C. under reduced pressure to constant weight to give 180 g of the expected Boc-pyrrolidine bis-amide as a white powder (75% yield).

53.2 g of Boc-pyrrolidine bis-amide (95.7 mmol, 1 equiv.) were added at room temperature, in portions to a solution consisting of 160 ml water and 160 ml 37% $HCl_{aq}$ (20 equiv.). After completion of the reaction (ca 30 min., HPLC in process control), the resulting solution was added over 1 h to a hot (50° C.) solution consisting of 197 g sodium bicarbonate (24.5 equiv.), 320 ml water, 530 ml ethyl acetate and 23 g 2,2-difluoroethyl triflate (1.1 equiv.). The addition funnel was washed with 15 ml water. After completion of the reaction (ca 30 min., HPLC in process control), the reaction mixture was cooled to RT. The aqueous phase was separated and re-extracted with 530 ml ethyl acetate. The organic phases were washed sequentially with 265 ml half saturated NaCl solution. The combined ethyl acetate phases were dried over $Na_2SO_4$ and filtered. The $Na_2SO_4$ filter cake was washed with 230 ml ethyl acetate. After solvent exchange to ethanol and crystallization at room temperature overnight, the resulting suspension was cooled to −20° C. After 1 h at −20° C., the suspension was filtered and washed in portions with in total 100 ml cold (−20° C.) ethanol. The crystals were dried to constant weight (50° C./reduced pressure) to give 40 g of a white powder (78% yield).

Example 2

Alternative Route to Obtain Boc-Pyrrolidine Intermediate 4 by Cycloaddition/Boc Protection 1. New [3+2] Cycloaddition

Step 8-9: Boc Deprotection/Alkylation

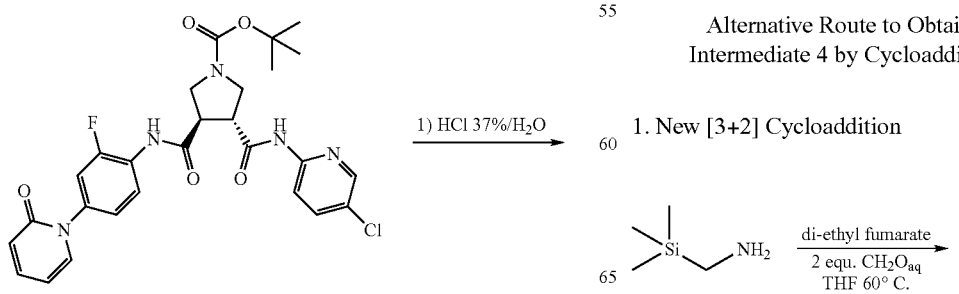

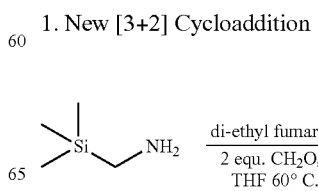

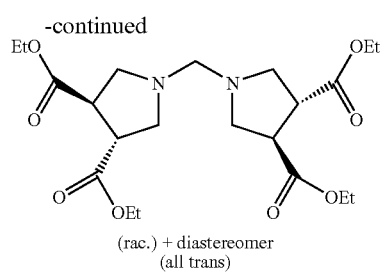

(rac.) + diastereomer
(all trans)

50 g of trimethylsilylmethylamine (475 mmol, 1 equiv.) were dissolved in 500 ml THF and treated at room temperature with 71.7 ml 37% aqueous formaldehyde (2 equiv.). After 15 min. at this temperature, the resulting solution was added over 10 min. to a 60° C. hot solution of 83.4 ml diethyl fumarate in 500 ml THF. The reaction mixture was refluxed overnight. The reaction mixture was cooled to room temperature and concentrated to dryness. The residue was re-dissolved in 1 l MTBE and extracted with 500 ml 1M HCl$_{aq}$. 500 ml MTBE were added to the aqueous phase followed by the addition of 500 ml 1M NaOH under vigorous stirring. The aqueous phase was separated and re-extracted with 250 ml MTBE. The combined organic phases were washed with 250 ml saturated aqueous NaCl solution, dried over MgSO$_4$, filtered and concentrated to dryness to give 83.3 g of the crude cycloadduct aminal as an oil (80% yield). The product may contain some amount of the hydrolyzed aminal.

2. Direct Boc-Protection from Aminal

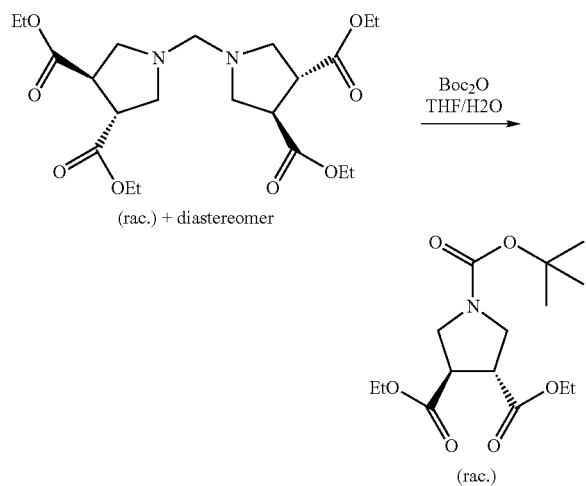

79.8 g of cycloadduct aminal from the previous step (180 mmol, 1 equiv.) were dissolved in 798 ml THF. 320 ml water and 86.8 g di-t-butyl-dicarbonate (2.16 equiv.) were added successively under stirring, at room temperature. The clear bi-phasic reaction mixture was stirred overnight (TLC in process control) at room temperature. After completion of the reaction, 225 mg DMAP were added to destroy excess of di-t-butyl-dicarbonate. The THF was evaporated under reduced pressure and 1 l MTBE was added. The crude product solution was washed with 0.8 l 1N HCl$_{aq}$. The aqueous phase was re-extracted with 1 l MTBE. The combined organic phases were washed with 500 ml water, dried over MgSO$_4$ and concentrated to dryness to give 96.6 g of the expected Boc-protected pyrrolidine as an oil (87% yield).

Alternatively, the Boc protection can be performed in a MTBE/water mixture allowing an easy, direct extraction. However, in this case Boc$_2$O quench with DMAP is not possible as described above. This is however no issue since the crude product can be directly used in the following enzymatic step as described in Example 1: step 4 resolution with Lipolase.

Example 3

Enzymatic Route B

Step 1: Cycloaddition

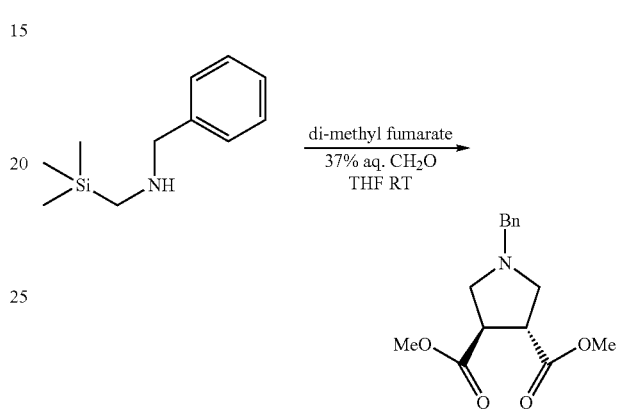

180 g N-benzyl-trimethylsilylmethyl-amine (903 mmol, 1 equiv.) were dissolved in 1.25 l THF and treated with 87.2 ml 37% aqueous formaldehyde (1.28 equiv.). After 15 min at room temperature, a suspension of 134 g dimethylfumarate (1 equiv.) and 1.4 ml trifluoroacetic acid (0.02 equiv.) in 625 ml THF was added. The reaction mixture was stirred until completion (GC in process control, ca 5 h) keeping the temperature between 20 and 35° C. 1 l heptane were added, followed by a mixture of 966 ml 1M HCl$_{aq}$ and 200 ml water. The organic phase was separated and extracted with a mixture of 450 ml 1M HCl$_{aq}$ and 1 l water. 1 l MTBE was added to the combined aqueous phases, followed by 150 ml 32% NaOH$_{aq}$ under vigorous stirring. The aqueous phase was separated and re-extracted with 1 l MTBE. The combined organic phases were washed with 500 ml water, dried over MgSO$_4$, filtered and concentrated under reduced pressure to give 238 g of cycloadduct as a yellow oil (95% yield).

Step 2: De-Benzylation

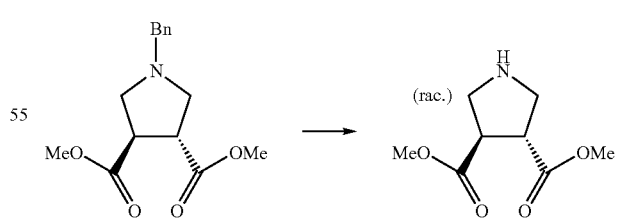

235 g of the N-benzylpyrrolidine was dissolved in 2.35 l MeOH and hydrogenated at room temperature, under atmospheric hydrogen pressure in the presence of 47 g 20% Pd(OH)$_2$/C. After completion of the reaction, the catalyst was filtered off and the filtrate was concentrated to dryness under reduced pressure to give 147.7 g of amine (93% yield). Alternatively, Pd on charcoal can also be used.

Step 3: Alkylation

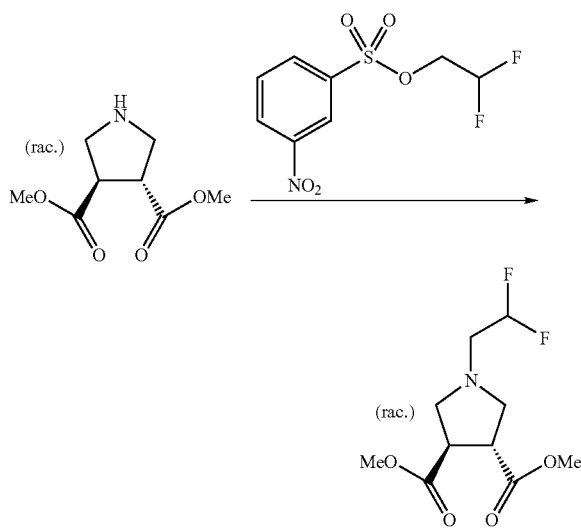

125 g of amine (668 mmol, 1 equiv.) were dissolved in 625 ml acetonitrile. 178 g of difluoroethyl 3-nitrobenzensulfonate (1 equiv.) and 114 ml ethyldiisopropylamine (1 equiv.) were added. The reaction mixture was heated to reflux until completion of the reaction (GC in process control, ca 20 h). The reaction mixture was cooled to room temperature and concentrated to dryness. 500 ml MTBE and 250 ml 10% aqueous $Na_2CO_3$ were added. The organic phase was separated and washed twice with 25% aqueous $NH_4Cl$ solution. The aqueous phases were re-extracted sequentially with 500 ml MTBE. The organic phases were combined, dried over $Na_2SO_4$, filtered and concentrated to dryness to give 162.8 g of difluoroethyl amine product (84% yield, ca 86a % by GC).

The product can be purified if required or used directly in next step.

Step 4: Enzymatic Resolution

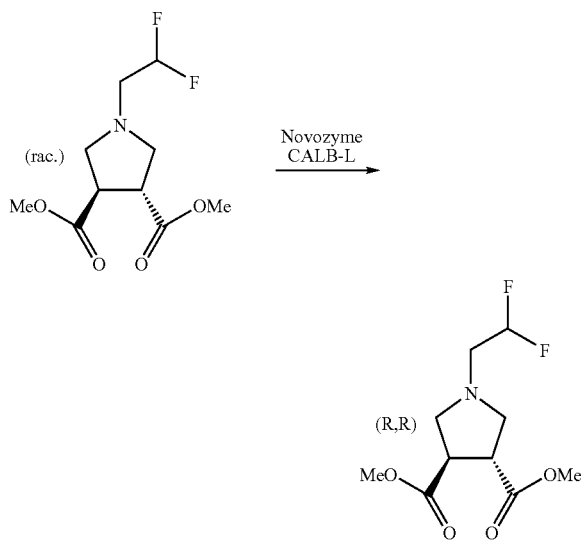

Example a):

132.5 g of (rac)-trans-dimethylester (454 mmol, 1 equiv., 86% pure by GC) was stirred in 1.2 l 0.05M aqueous magnesium acetate pH 6 solution. The pH of the resulting emulsion (pH 8.2) was adjusted to 6.5 by addition of acetic acid. 9.7 ml of Novozyme CALB L (Novozyme) were then added, triggering the reaction. The pH was kept constant at 6.5 by the automated addition of 1M NaOH (pH-stat). After completion of the reaction (targeted e.e. reached, typically >99% e.e., ca 90 h reaction time, 0.57 equiv. NaOH added, GC in process control), 1 l dichloromethane was added. The pH was adjusted to 7. The aqueous phase was separated and re-extracted three times with 1 l dichloromethane. The organic phases were washed with 400 ml saturated $NaHCO_3$ solution and 400 ml water. The organic phases were combined, dried over $Na_2SO_4$, filtered and concentrated to dryness under reduced pressure to give 64.2 g of crude (R,R)-diester (49% yield, 88% pure by GC).

Example b):

500 g of (rac)-trans-dimethylester (1.839 mol, 1 equiv., 92.4% pure by GC) were stirred in 4.5 l 0.05M aqueous magnesium acetate pH 6 solution. The pH of the resulting emulsion was adjusted to 6.5 by addition of acetic acid. 40 ml of Novozymes CALB L (Novozyme) were then added, triggering the reaction. The pH was kept constant at 6.5 by the automated addition of 1M NaOH (pH stat). After completion of the reaction (targeted e.e. reached, typically >99% e.e., ca 69 h reaction time, 0.55 equiv. NaOH added, GC in process control), 100 ml dichloromethane was added. 1 kg of sodium chloride was added and the reaction mixture extracted twice with 5 l MTBE. The combined organic phases were washed with 2 l saturated $NaHCO_3$ solution and 2 l water. The organic phase was dried over $Na_2SO_4$, filtered and concentrated to dryness under reduced pressure to give 215.5 g of crude (R,R)-diester (43% yield, 92% pure by GC).

Step 5: Enzymatic Monohydrolysis

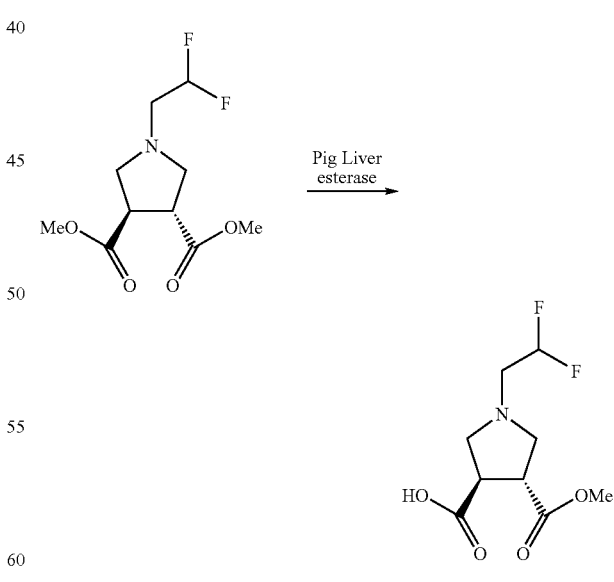

Example a):

63.1 g of crude (R,R)-diester were stirred in 730 ml of 0.1M aqueous NaCl solution/3.8 M sodium phosphate pH 7 buffer solution. To the resulting emulsion were added 210 µl of technical grade pig liver esterase (Technical grade; Catalogue No. 10491228; Roche Applied Sciences) at room temperature. The pH was kept at 7.0 by the automated addition of 1M NaOH$_{aq}$. After completion of the reaction (240 ml 1M NaOH consumed, ca 75 h reaction time, GC in process control), 1 l dichloromethane was added. The organic phase was separated and discarded. The pH of the aqueous phase was adjusted to 3.5 by the addition of 25% HCl$_{aq}$. The aqueous phase was extracted with 1 l ethyl acetate. The pH adjustment and extraction steps were repeated 4 times. The combined organic phases were dried over Na$_2$SO$_4$, filtered and concentrated to dryness to give 41.8 g of mono acid mono ester (98% pure by GC, 78% yield).

Example b):

In a 750 ml four-necked flask equipped with a mechanical stirrer, thermometer, pH-probe and a titrating agent inlet connected to a pH-stat, 38 g (R,R)-diester (141.3 mmol; GC-purity 93.4%) was emulsified in 340 ml 0.1 M sodium chloride/3.8 mM sodium phosphate buffer pH 7.0 under vigorous stirring. The reaction was started by adding 240 ul pig liver esterase (Technical Grade, 3.12 MU/L; Roche Applied Sciences), and the pH was kept constant at 7.0 by the automated addition (pH-stat) of 1.0 M NaOH-solution under vigorous stirring. After a consumption of 137.3 ml 1.0 M NaOH-solution (137 mmol, 97.2% conversion, after 46 h) the reaction was stopped by the addition of 20 ml dichloromethane and washed with 760 ml MTBE. The aqueous phase was set to pH 3.6 by addition of 139 ml concentrated sodium phosphate solution (63 ml phosphoric acid to 76 ml 28% NaOH) and extracted with 3×760 ml ethyl acetate. The combined ethyl acetate phases were dried over sodium sulfate, filtered, evaporated and dried to give 29.4 g (R,R)-monoacid (86%) as a white solid.

Crystallization of crude mono acid mono ester: 56.37 g crude mono acid mono ester were dissolved in 200 ml ethyl acetate with heating. The solution was cooled to room temperature and 400 ml heptane were slowly added. The turbid solution was seeded. After 1 h at room temperature, the suspension was filtered. The filter cake was dried at 45° C. under reduced pressure to give 46.82 g of a white powder. The mother liquors were evaporated and re-dissolved in 20 ml ethyl acetate. 60 ml heptane were added. After 3 h at room temperature, the suspension was filtered. The filter cake was dried at 45° C. under reduced pressure to give 7.12 g of a white powder. In total 53.94 g mono acid monoester were isolated.

Step 6: First Amide Coupling

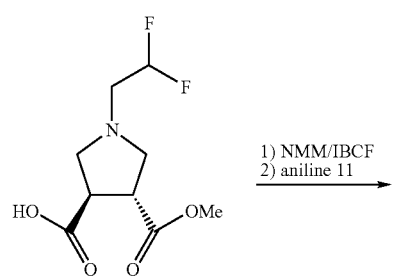

1) NMM/IBCF
2) aniline 11

-continued

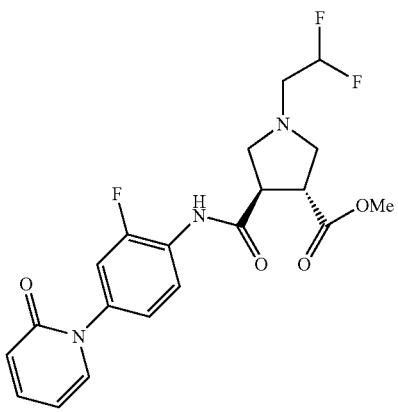

Example a):

1 g mono acid mono ester (4.2 mmol, 1 equiv.) were dissolved in 3 ml THF together with 465 ul N-methylmorpholine (1 equiv.). This solution was added dropwise over 20 min to a cold 0-5° C. solution of 575 ul isobutyl chloroformate in 5 ml THF. After 1 h at 0-5° C., 181 mg lithium chloride (1 equiv.) were added followed by 861 mg of fluoroaniline (1 equiv.). The reaction mixture was stirred at room temperature until completion of the reaction (HPLC in process control, ca 1-3 h). 7 ml water, 20 ml ethyl acetate and 10 ml 1M HCl$_{aq}$ were added. The organic phase was separated and re-extracted with 10 ml 1M HCl$_{aq}$. The pH of the combined aqueous phases was adjusted to 9-10 by addition of saturated Na$_2$CO$_3$ and extracted twice with 50 ml ethyl acetate. The combined organic phases were dried over MgSO$_4$, filtered and concentrated to dryness under reduced pressure to give 1.72 g of amide ester (96% pure by HPLC, 96% yield).

Example b):

20 g of the mono acid mono ester (84.3 mmol, 1 equiv.) were dissolved in 60 ml THF together with 9.29 ml N-methylmorpholine (1 equiv.). The resulting solution was added dropwise over 20 min to a cold (0-5° C.) solution of 11.49 ml isobutyl chloroformate (1 equiv.) in 100 ml THF. After 1 h at 0-5° C. (this hold time can be shorter since the activation feed controlled), 17.22 g of the fluoroaniline (1 equiv.) were added followed by 3.57 g lithium chloride (1 equiv.). The reaction mixture was warmed to RT. After 3 h reaction, 140 ml water, 400 ml ethyl acetate and 200 1M HCl were added. The organic phase was separated and re-extracted with 200 ml 1M HCl. The aqueous phases were combined and the pH was adjusted to ~10 by addition of 160 ml saturated aqueous Na$_2$CO$_3$. The resulting mixture was extracted twice with 400 ml ethyl acetate. The organic phases were combined, dried over MgSO$_4$, filtered and concentrated under reduced pressure to a volume of ca 140 ml (crystallization may already start). 420 ml heptane were slowly added. The resulting suspension was stirred 3 h at RT and filtered. The filter cake was dried under reduced pressure to give 31.1 g of product (87% yield).

Step 7: Second Amide Coupling

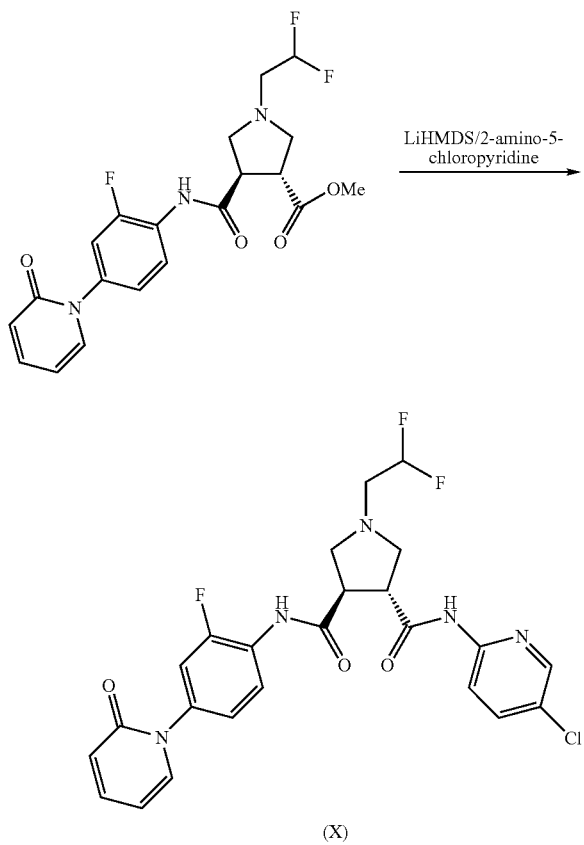

Example a):

465 mg of 5-chloro-2-amino pyridine (1.5 equiv.) were dissolved in 8 ml THF, together with 1 g of amide ester (2.36 mmol, 1 equiv.). The solution was cooled to 0-2° C. and 7.1 ml of a 1M LiHMDS solution in THF (3 equiv.) were added dropwise. After completion of the reaction (ca 2 h, HPLC in process control), the pH was adjusted to 3.5 by addition of 2M $HCl_{aq.}$ (ca 6 ml, 5 equiv.). The reaction mixture was extracted twice with 15 ml ethyl acetate. The organic phases were washed sequentially with 13 ml water. The combined organic phases were dried over $MgSO_4$, filtered and concentrated to dryness under reduced pressure to give 1.27 g crude compound of formula (X).

Example b):

13.94 g of 2-amino-5-chloropyridine (1.5 equiv.) and 30 g mono ester mono amide (70.85 mmol, 1 equiv.) were dissolved in 240 ml THF. The solution was cooled to 0-2° C. and 212.6 ml 1M LiHMDS solution in THF (3 equiv.) was added over 20 min. After 1.5 h reaction (in process control by HPLC), 245 ml 2M $HCl_{aq}$ were added over 15 min keeping the temperature between 0-10° C. (pH of resulting mixture: 3.2). The resulting mixture was extracted twice with 350 ml ethyl acetate. The organic phases were washed sequentially with 200 ml half saturated $NaCl_{aq}$, combined, dried over $Na_2SO_4$, filtered and concentrated under reduced pressure to give crude product which was then purified by crystallized from a 1:2 ethanol/heptane mixture (85% yield).

Branch 1: Difluoroethyl 3-nitro-benzenesulfonate

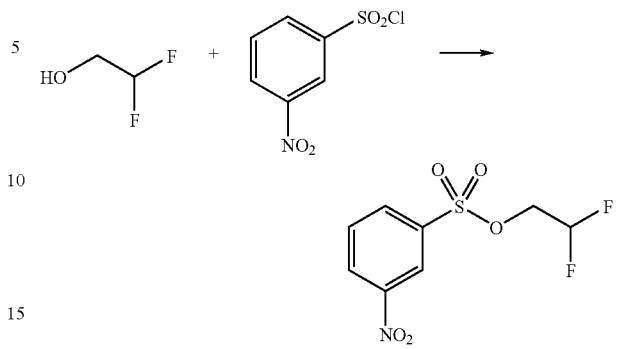

194 g 3-nitro-benzenesulfonyl chloride (1.13 equiv.) were charged in the reaction vessel followed by 1.3 l isopropyl acetate and the solution was cooled to 0-5° C. A solution of 65 g 2,2-difluoroethanol (753 mmol, 1 equiv.), 163 ml triethylamine (1.55 equiv.) and 325 ml isopropyl acetate was added dropwise over 30 min, keeping the temperature between 0-5° C. After 4 h reaction (HPLC in process control), the reaction mixture was washed with 650 ml water. The water phase was re-extracted with 650 ml isopropyl acetate. The organic phases were washed with 650 ml 1M $HCl_{aq}$ and 650 ml 10% $NaCl_{aq}$ solution. The organic phases were combined, dried over $MgSO_4$, filtered and concentrated to dryness under reduced pressure to give 196 g 2,2-difluoroethyl 3-nitrobenzenesulfonate (97% yield) as a viscous oil which crystallized on standing. The product can also be crystallized from isopropanol (seeding at 30° C., concentration: ca 13 L/kg product).

Branch 2: Fluoroaniline Method A:

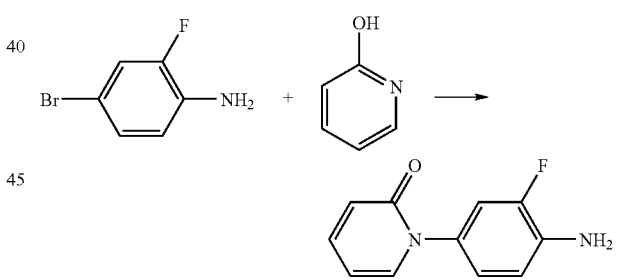

44 g of 4-bromo-2-fluoroaniline (229 mmol, 1 equiv.), 31.5 g, 2-hydroxypyridine (1.4 equiv.), 34.80 g potassium carbonate (1.1 equiv.), 6.55 g copper (I) iodide (0.15 equiv.) were charged in the reaction vessel followed by 100 ml N,N-dimethylacetamide. The suspension was heated at 155° C. (jacket temperature) for 4 h (HPLC in process control). The reaction mixture was cooled to 120° C. (jacket temperature), 400 ml water were added over 30 min and the reaction mixture was slowly cooled down to room temperature. After 30 min, the reaction mixture was cooled to 0-5° C., kept at this temperature for 1 h and filtered. The filter cake was washed with 200 ml water (0-5° C.) and the crystals were dried overnight at 70° C. under reduced pressure to give 43.1 g of crude product. The crude product was suspended in 1 l ethanol together with 5 g active charcoal Norit SX-3 and heated at reflux for 30 min. The hot suspension was filtered on a pressure filter (with charcoal plate). The filter cake was washed with 200 ml hot ethanol. The filtrate was concentrated to ca 500 ml at 60° C. under ca 180 mbar. The suspension was then stirred at room temperature during 30 min, followed by 30 min at 0-2° C. and was finally filtered. The crystals were washed in portions with cold 0° C. ethanol, in total 50 ml and were dried at 60° C. under reduced pressure until constant weight to give 33.9 g product (72% yield).

Branch 2: Fluoroaniline Method B:

50 g (263 mmol) of 4-bromo-2-fluoroaniline, 25 g (263.1 mmol) 2-hydroxypyridine and 19.4 g (0.5 equiv.) copper (I) oxide were charged in the reaction vessel. 100 ml pyridine were added and the suspension was heated at reflux during 14 h (HPLC in process control, <3a % 4-bromo-2-fluoroaniline). 100 ml pyridine were added to the dark reaction mixture keeping the temperature between 85-95° C. 200 ml water were added over 15-30 min at 85-95° C. The dark solution was cooled to 0° C. over 3 h (if crystallization does not spontaneously occur at 40° C., the solution is seeded with 0.5 g seed crystals at 40° C.—seeding can be repeated between 30-40° C. if necessary). The dark suspension was stirred 30 min to 1 h at 0° C. and filtered. The filter cake was washed 3 times with 100 ml cold (4-10° C.) water. The crystals were dried at 60-65° C. under reduced pressure until constant weight to give 28.9 g of product (94% m/m purity, 50% yield). In case where crude product quality is not suitable it can be upgraded by a charcoal treatment in hot MeOH followed by a hot filtration and a crystallization in MeOH.

Branch 2: Fluoroaniline Method C:

3.0 g (15.8 mmol) of 4-bromo-2-fluoroaniline, 1.5 g (15.8 mmol. 1.0 equiv.) 2-hydroxypyridine, 0.47 g (3.16 mol, 0.2 equiv.) copper (I) oxide, 347 μl (3.16 mmol, 0.2 equiv.) N,N'-dimethylethylene diamine and 2.4 g (17.4 equiv., 1.1 eq) potassium carbonate were charged into the reaction vessel. 34 ml toluene were added and the suspension was heated at reflux during 16 h (HPLC in process control, <1a % 4-bromo-2-fluoroaniline). 10 ml toluene were added to the dark reaction mixture keeping the temperature between 85-95° C. 45 mL water were added over 15-30 min at 85-95° C. The dark solution was crystallized by cooling to 0° C., stirred 30 min to 1 h at 0° C. and filtered. The filter cake was washed 3 times with 25 ml cold (4-10° C.) water. The crystals were dried at 60-65° C. under reduced pressure until constant weight to give 3.0 g of product (79% m/m purity, 75% yield).

In case where crude product quality is not suitable it can be upgraded by a charcoal treatment in hot MeOH followed by a hot filtration and a crystallization in MeOH.

Branch 2: Fluoroaniline Method D:

20 g of 4-bromo-2-fluoroaniline (103 mmol, 1 equiv.) and 15.16 g (155 mmol, 1.5 equiv.) 2-hydroxypyridine were charged in the reaction vessel, followed by 40 ml dimethylacetamide. 15.7 g (1.1 equiv.) potassium carbonate and 760 mg (0.05 equiv.) Cu₂O were added. The suspension was heated at 130° C. during 18 h (HPLC in process control). 70 ml N,N-dimethylacetamide were added. The reaction mixture was cooled to 100° C. 60 ml water were added and the reaction mixture was slowly cooled to room temperature (crystallization started at ca 40° C., seeding can be done if necessary). The pH was adjusted to 8 by addition of 27 ml 2 M aqueous HCl. The suspension was cooled to 0° C. and stirred 2 h at 0° C. The suspension was filtered and the filter cake was washed with 50 ml water and 80 ml MTBE. The crystals were dried at 60° C. until constant weight to provide 15.2 g of product (93a % ca 67% yield).

In case where crude product quality is not suitable it can be upgraded by a charcoal treatment in hot MeOH followed by a hot filtration and a crystallization in MeOH.

Branch 2: Fluoroaniline Method E:

Step 1:

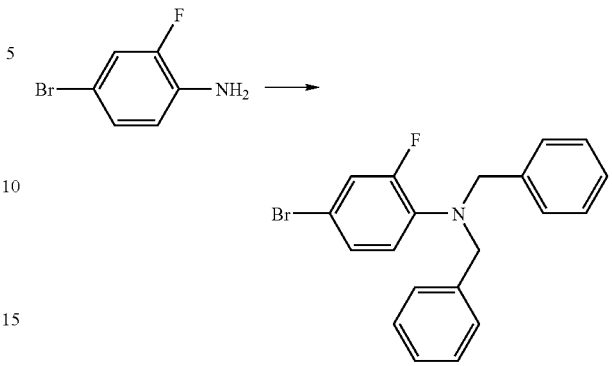

10 g of 4-bromo-2-fluoroaniline (51.6 mmol, 1 equiv.), 8.26 g Na₂CO₃ (1.5 equiv.) and 60 ml DMF were charged in the reaction vessel followed by 13.13 ml benzyl bromide (2.1 equiv.). The reaction mixture was heated to 100-110° C. for about 2-4 h (HPLC in process control) and was then cooled to room temperature. The reaction mixture was added to a mixture of 120 ml water and 200 ml MTBE (under stirring). The organic phase was separated, washed with 120 ml water, dried over MgSO₄ and filtered. The solvent was exchanged to heptane with a final concentration of ca 1:3 m/v product/heptane. The resulting mixture was heated at ca 70° C., cooled to room temperature then to 0° C. for 1 h. The resulting white suspension was filtered, washed with cold (0-5° C.) heptane and dried until constant weight (50° C./5-10 mbar) to give 14.4 g of an off-white powder.

Step 2:

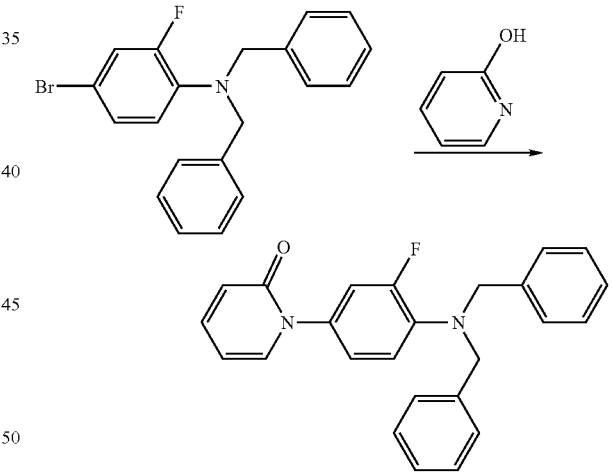

20 g of the dibenzylaniline (48.64 mmol, 1 equiv.) were dissolved in 40 ml N,N-dimethylacetamide at room temperature. 7.15 g 2-hydroxypyridine (1.5 equiv.), 717 mg Cu₂O (0.1 equiv.) and 7.39 g K₂CO₃ (1.1 equiv.) were added sequentially. The reaction mixture was heated to 130° C. ca 23 h (HPLC in process control) and then cooled to room temperature. 100 ml dichloromethane and 200 ml 2M HCl were added. The organic phase was separated and washed with 200 ml 2M HCl. The aqueous phases were extracted with 100 ml dichloromethane. The combined organic phases were dried over MgSO₄ and concentrated at 45° C. under reduced pressure until constant weight. The resulting crude solid (ca 20 g) was heated in 150 ml AcOEt until dissolution. 100 ml heptane were slowly added until obtention of a turbid solution. The mixture was slowly cooled to room temperature. After ca 30 min, crystallization started (if not starting, seeding can be performed). After an additional 1 h stirring at room temperature, the suspension was filtered. The filter cake was washed with 40 ml of a 1:1 mixture of heptane and AcOEt and dried until constant weight at 50° C. under reduced pressure to give 16 g of an off-white powder (83% yield).

Step 3:

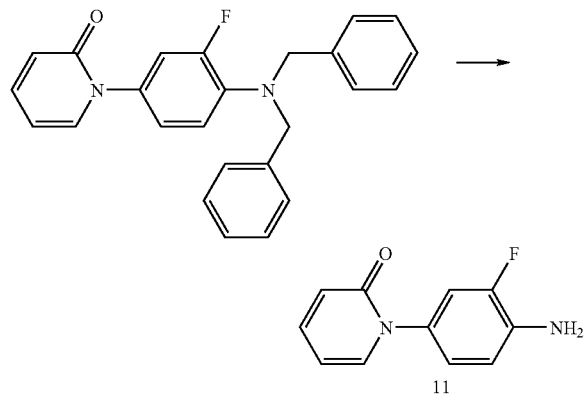

11

4 g of the dibenzylamine were dissolved in a mixture of 80 ml MeOH and 80 ml AcOEt. 400 mg 5% Pd/C (Johnson Matthey) were charged. The hydrogenation was performed at room temperature under atmospheric pressure of H$_2$. The hydrogenation is monitored by gas uptake and HPLC in order to avoid overhydrogenation (of the pyridone ring). After completion of the reaction, the reaction mixture was filtered to remove the catalyst and the filter cake was washed with 40 ml MeOH. The filtrate was concentrated under reduced pressure to give 2 g of crude product. 25 ml MeOH were added and the mixture was heated until complete dissolution. The solution was cooled to RT and stirred for 4 h. The resulting suspension was filtered. The filter cake was washed with 2 ml cold (0-5° C.) MeOH and dried at 50° C. under reduced pressure until constant weight to give 1.5 g of an off-white powder (72% yield).

Example 4

Alternative Route to Convert Amide Ester to Compound (X) by Deprotection/Free Base Formation/Alkylation/Amide Formation Step 1: Boc Deprotection

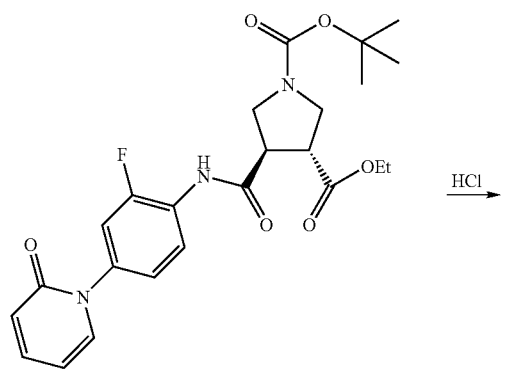

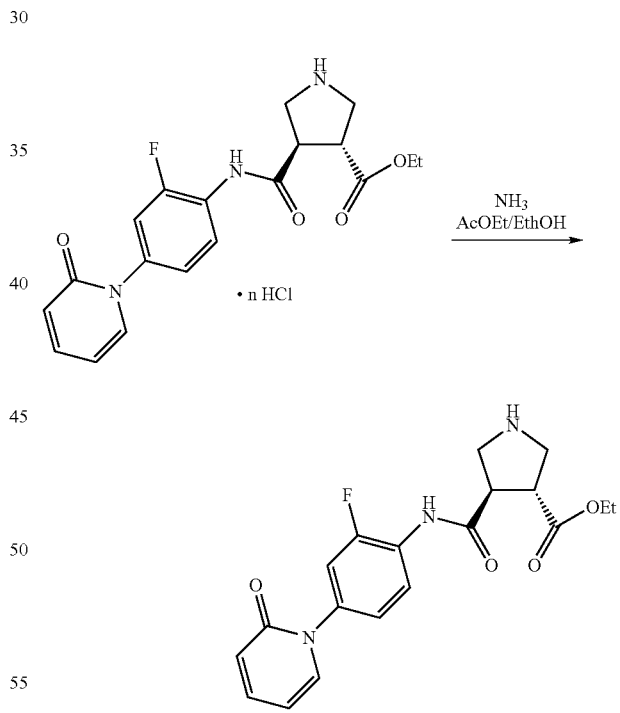

15 g of crude Boc-pyrrolidine (31.68 mmol, 1 equiv.) were dissolved in 150 ml ethanol. 13.64 ml acetyl chloride (6 equiv.) were added over 20 min at room temperature. After 20 h reaction, during which a suspension formed, 150 ml MTBE were added over 5 min. After 90 min, the suspension was filtered and the filter cake was dried under reduced pressure at 45° C. to give 12.07 g of hydrochloride (ca 2-3HCl., ca 90% yield).

Step 2: Free Base Formation 1.79 g (4 mmol, 1 equiv., taken as a bis hydrochloride salt, n=2) hydrochloride (see previous step) were suspended in a mixture of 50 ml AcOEt and 9 ml ethanol. 10 ml of a 5M ethanolic NH$_3$ solution (20 mmol, 5 equiv.) were added and the suspension was stirred 70 h at room temperature and filtered. The filtrate was concentrated under reduced pressure to provide 1.5 g of the free amine (quant. yield).

Alternatively, the amine hydrochloride can be liberated by extraction under basic pH.

Step 3: Alkylation

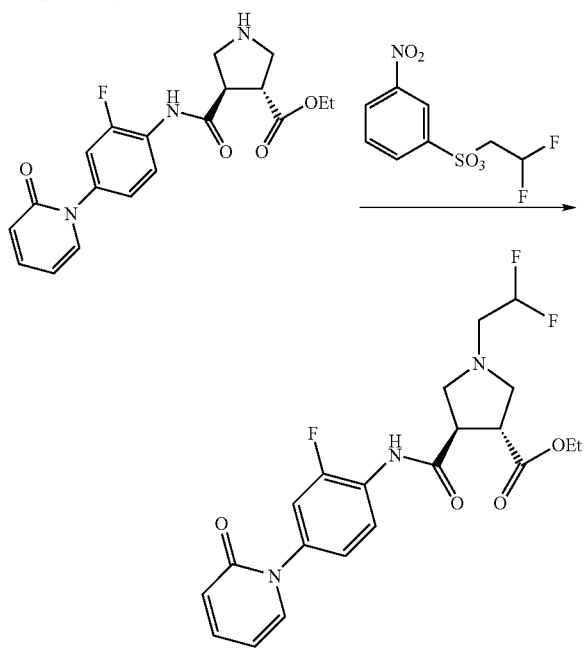

3 g (8 mmol, 1 equiv.) of amine were dissolved in 15 ml acetonitrile together with 2.39 g (1 equiv.) of difluoroethyl-3-nitro-benzenesulfonate and 1.5 ml (1.1 equiv.) ethyl-diisopropylamine. The solution was heated at 80° C. during 22 h (HPLC in process control). The reaction mixture was cooled to room temperature and concentrated under reduced pressure. The residue was re-dissolved in 30 ml AcOEt. 15 ml 10% aqueous $K_2CO_3$ were added. The mixture was filtered. The organic phase from the biphasic filtrate was separated and washed twice with 15 ml 10% aqueous $K_2CO_3$. The aqueous phases were re-extracted sequentially with 30 ml AcOEt. The organic phases were combined, dried over $MgSO_4$ and concentrated under reduced pressure to a volume of ca 10 ml. 35 ml MTBE were slowly added, leading to a turbid solution. The latter was seeded and stirred 1 h at room temperature and partially concentrated upon which crystallization started. After 2 h stirring at room temperature, the suspension was filtered. The filter cake was dried at 45° C. under reduced pressure to provide 2.56 g of light yellow crystals (72% yield).

Alternatively, a) The product can also be purified for example by chromatography. b) aqueous $Na_2CO_3$ can also be used instead of the potassium carbonate solution during the extractions.

Step 4: Second Amide Formation

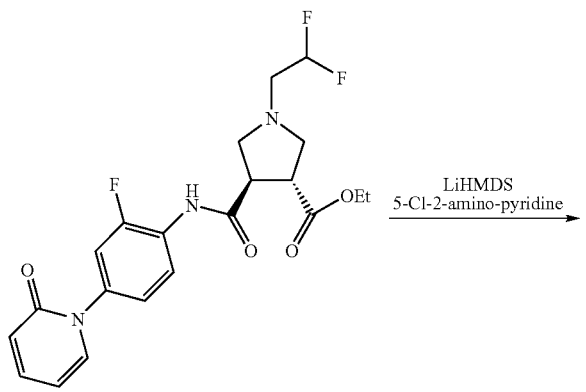

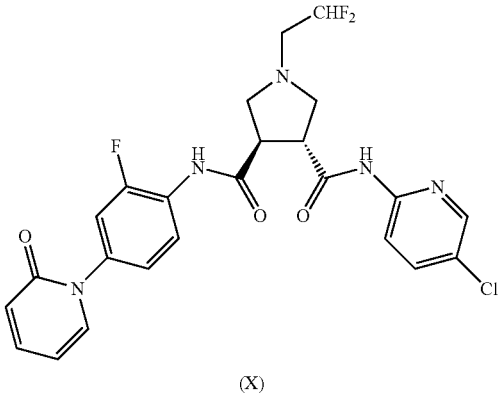

(X)

1.04 g (7.9 mmol, 1.5 equiv.) 5-chloro-2-aminopyridine, 2.3 g (5.3 mmol, 1 equiv.) amide ester and 18.4 ml THF were charged in the reaction vessel and the resulting mixture was cooled to 0-5° C. 15.8 ml (3 equiv.) of 1M LiHMDS solution in THF were added over 20 min. After 3 h reaction (HPLC in process control), 18 ml (6.85 equiv.) 2M aqueous HCl were added (pH 3.3). The resulting mixture was extracted twice with 92 ml AcOEt. The organic phases were washed sequentially with 23 ml sat. aqueous NaCl solution, combined, dried over $MgSO_4$ and concentrated under reduced pressure to provide 2.78 g of crude product.

The product can be purified by chromatography or crystallization from EtOH or ethanol/heptane.

Example 5

Cyclic Anhydride Approach

Step 1: Cylcoaddition

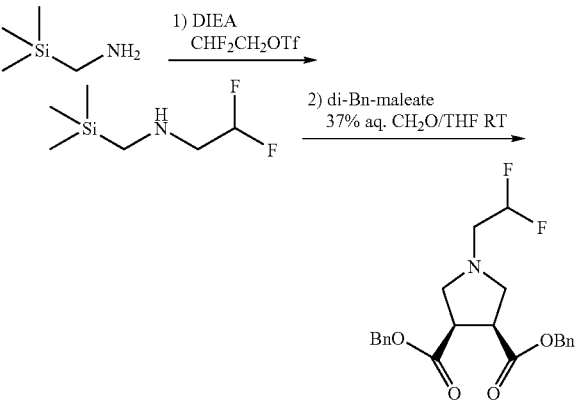

25 g of difluoroethyl triflate (117 mmol, 1 equiv.) were added dropwise at 20-25° C. to a solution of 16 ml trimethylsilylmethyl-amine (1 equiv.) and 20 ml ethyldiisopropylamine (1 equiv.) in 225 ml THF. After 2 h, the reaction mixture was treated with 11.46 ml 37% aqueous formaldehyde (1.3 equiv.). After 10 min. at room temperature, a solution consisting of 34.61 g dibenzyl maleate (1 equiv.), 12.5 ml THF and 913 ul trifluoroacetic acid (0.1 equiv.) was added. After 17 h reaction, the reaction mixture was concentrated to ca 80 ml. 125 ml MTBE and 104 ml 1M $HCl_{aq}$ (2.5 equiv.) were added. The aqueous phase was separated and re-extracted with 62.5 ml MTBE. The organic phases were washed with 125 ml water and 167 ml half saturated aqueous $NaHCO_3$ solution, combined, dried over $MgSO_4$, filtered and concentrated to dryness under reduced pressure to give 45.5 g of crude cycloadduct (ca 86% yield, contains ca 11% m/m dibenzyl maleate).

The crude product can be purified for instance by chromatography but is more conveniently introduced in the next step without purification.

Step 2: Hydrogenation

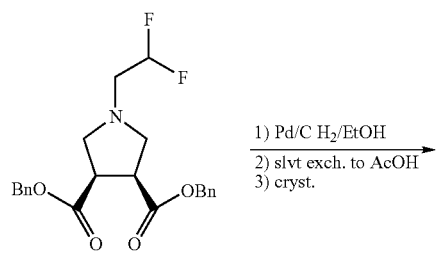

45.5 g of crude dibenzyl ester (100 mmol, 1 equiv, 89% pure m/m, see previous step) was dissolved in 364 ml ethanol followed by the addition of 32.15 ml triethylamine (2.3 equiv.) and 2.1 g 10% Pd/C. The dibenzyl ester was hydrogenated under atmospheric hydrogen pressure. After completion of the reaction, the catalyst was filtered off and 80.7 ml acetic acid were added followed by seed crystals. The ethanol was distilled off under reduced pressure at 40° C. (at 60° C. significative cis to trans isomerization is observed). The obtained suspension was stirred overnight at room temperature and filtered. The crystals were washed with 20 ml acetic acid, 60 ml MTBE and were dried under reduced pressure to give 14.6 g of bis-acid as a white powder (60% yield, contains ca 9% m/m residual acetic acid).

Step 3: Cyclic Anhydride Formation:

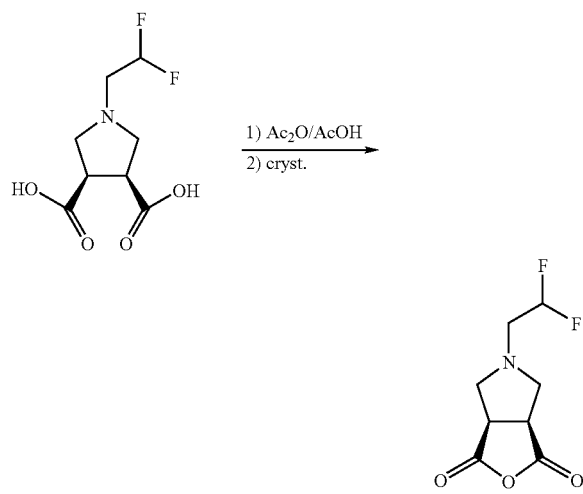

14.3 g of bis acid (58.6 mmol, 1 equiv., 92% m/m) were suspended in 143 ml acetic acid. 27.7 ml acetic anhydride (5 equiv.) were added and the reaction mixture was heated to 60° C. After 1 h, a solution was obtained. After 3 h, the reaction mixture was cooled to room temperature and concentrated to a colorless oil to which 50 ml diisopropyl ether was added. The solution was seeded. After 1 h stirring at room temperature, the suspension was filtered. The crystals were washed with diisopropyl ether and dried at 50° C. under reduced pressure to give 7.8 g of anhydride as a white powder. The mother liquors were concentrated to dryness and the residual oil was treated with 50 ml diisopropyl ether and seed crystals, providing after filtration, washing and drying, a second crop of anhydride (3.2 g). Total yield: 91%.

Step 4: Cyclic Anhydride Opening:

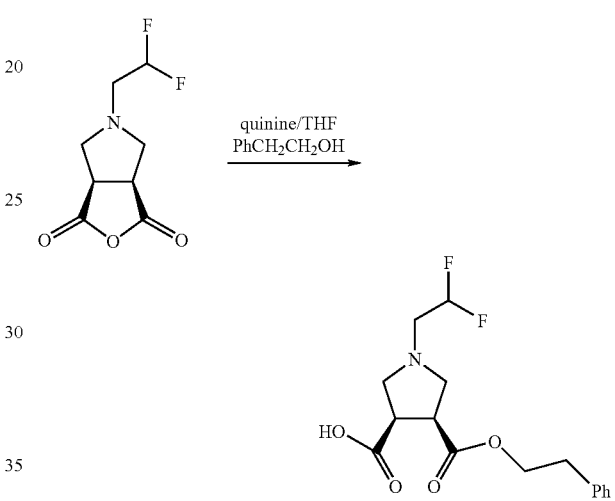

Example a)

A solution consisting of 16.94 g, quinine (1 equiv.) and 9.3 ml 2-phenylethanol (1.5 equiv.) in 120 ml THF was cooled to −20 to −15° C. A solution of 10.5 g of anhydride (51.2 mmol, 1 equiv.) in 30 ml THF was added dropwise. After 4 h reaction (HPLC in process control or in-line FTIR spectroscopy with a ReactIR iC10 system) the resulting suspension was warmed overnight to room temperature and concentrated to dryness to provide 43.5 g of a crude ester acid as quinine salt (92:8 d.r. by HPLC). The crude salt was suspended in a mixture of 50 ml isopropyl acetate and 50 ml water. The pH was adjusted to 1 by addition of 20 ml of 25% $HCl_{aq}$. The aqueous phase was separated and washed with 50 ml isopropyl acetate. The organic phases were re-extracted with 25 ml 1M HCl. The aqueous phases were combined, cooled to 0-2° C. and the pH was adjusted to 3.0 by addition of 32% $NaOH_{aq}$. The product started to crystallize. After 2 h stirring at 0-2° C., the suspension was filtered. The filter cake was washed with 50 ml cold 0-2° C. water and dried at 60° C. under reduced pressure to give 14.8 g of product as a white powder (88% yield, 95:5 d.r.).

Example b)

A solution of 40 g of anhydride (195 mmol, 1 equiv.) in 150 ml THF was added dropwise between −20 to −15° C. to a solution consisting of 71 g quinine (1.1 equiv.) and 36.1 g 2-phenylethanol (1.5 equiv.) in 750 ml THF. After reaction overnight (HPLC in process control or in-line FTIR spectroscopy with a ReactIR iC10 system) the resulting suspension was warmed to room temperature and 250 ml water were added. The THF was distilled off at 40° C. under reduced pressure. 125 ml MTBE were added to the resulting aqueous suspension and the pH was adjusted to ca 1 by addition of 125 ml 25% aqueous HCl. The aqueous phase was separated and washed with 125 ml MTBE. The organic phases were washed sequentially with 62.5 ml 1 M aqueous HCl. The acidic aqueous phases were combined and cooled to 0-5° C. The pH was adjusted to 3.0 by addition of 55 ml 32% NaOH$_{aq}$ upon which product precipitated out. The suspension was stirred 4 h at 0-5° C. and filtered. The filter cake was washed twice with 125 ml cold (0-5° C.) water and dried at 60° C. under reduced pressure until constant weight to give 59.9 g hemiester as a white powder (95:5 e.r., 98.7% w/w by quantitative HPLC, 93% yield).

Step 5: Epimerization

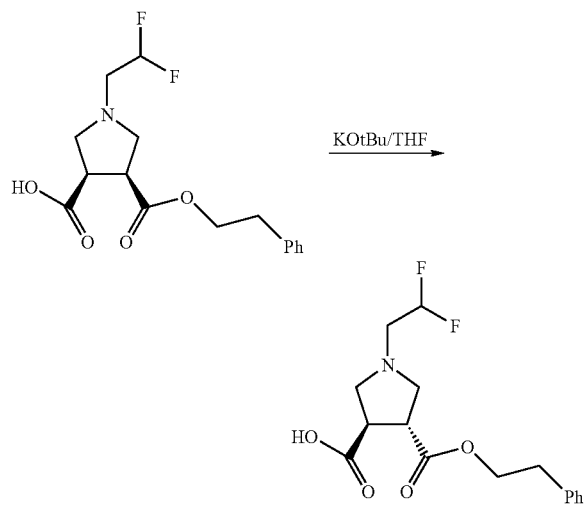

Example a)

10.6 g (cis)-acid ester (32.4 mmol, 1 equiv.) were dissolved in 212 ml THF (it is important to have a solution). The solution was cooled to −70° C. and 5.56 g potassium t-butoxide (1.5 equiv.) were added. After 30 min reaction (HPLC in process control), 9.3 ml acetic acid (5 equiv.) were added. The reaction mixture was added to 100 ml water (pH 6.5) and the pH was adjusted to 3.0 by addition of 1M HCl (ca 60 ml 1.85 equiv.). The THF was removed under reduced pressure at 40° C. upon which crystallization started. The white suspension was stirred 30 min. at room temperature and filtered. The filter cake was washed with cold water. The crystals were dried at 50° C. under reduced pressure to give 8.0 g of trans-ester mono acid as a white powder (76% yield, >99% trans: <1% cis).

Alternatively, the reaction can be quenched by addition of HCl$_g$ in dioxane.

It is important to obtain a solution prior to KOtBu addition. Indeed, some precipitation have sometimes been observed during cooling of the starting material solution to −70° C. In these cases, we later showed that the starting material solubility was so low that it did not react completely, providing low trans/cis selectivities. Here is an improved process circumventing this problem. The starting material can be kept in solution in THF by formation of an appropriate soluble amine salt, for example its triethylamine salt:

Example b)

50 g of cis-monoacid mono ester (151 mmol, 1 equiv.) were charged in the reaction vessel, followed by 850 ml THF and 21 ml triethylamine (1 equiv.). The resulting solution was cooled to −70° C. and a solution of 25.9 g KOtBu (1.5 equiv.) in 100 ml THF was added dropwise maintaining the temperature<−65° C. After 45 min reaction (in process control by HPLC), the reaction was quenched by addition of 12.9 ml acetic acid (1.5 equiv.). The reaction mixture was warmed to room temperature and 250 ml water were added (resulting pH ca 7.8). The THF was distilled off at 40° C. under reduced pressure. 300 ml ethyl acetate were added and the pH was adjusted to 3.0 by addition of HCl 2 M (ca 180 ml, 2.4 equiv.). The aqueous phase was separated and re-extracted with 150 ml ethyl acetate. The organic phases were washed with 250 ml water, combined, and concentrated at 40° C./ca 150 mbar to ca 250 ml. 500 ml heptane were added and the suspension was heated to reflux until dissolution. The heating was stopped and the solution was slowly cooled to room temperature during which crystallization started. After stirring overnight at room temperature, the suspension was filtered. The filter cake was washed with 200 ml of a 1:2 ethyl acetate/heptane mixture and dried at 50° C. under reduced pressure until constant weight to give 42.5 g of trans hemiester as a white powder (86% yield, e.r. and d.r.>99:<1 by HPLC, below the detection limit).

Step 6: First Amide Coupling

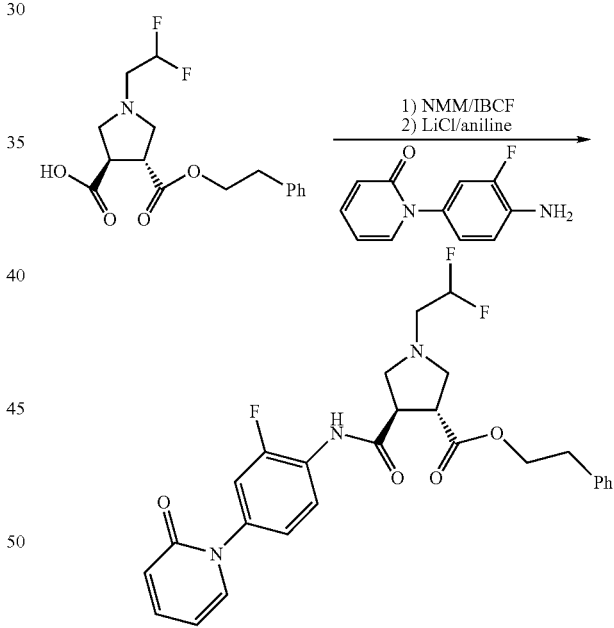

Example a)

500 mg of trans-acid ester (1.58 mmol, 1 equiv.) were dissolved in 1.5 ml THF together with 168 ul N-methylmorpholine (1.0 equiv.). This solution was added to a cold 0-5° C. solution of 208 ul isobutyl chloroformate (1 equiv.) in 2.5 ml THF. After 30 min reaction, 65 mg lithium chloride (1 equiv.) were added followed by 312 mg of aniline (1 equiv.). The reaction mixture was then stirred 2 h at room temperature (TLC or HPLC in process control). 3.5 ml water, 15 ml ethyl acetate and 5 ml 1M HCl$_{aq}$ were added. The organic phase was separated and re-extracted with 3.6 ml 1M HCl$_{aq}$ and was discarded. The pH of the combined aqueous phases was adjusted to 9-10 by addition of 1.5 ml Na$_2$CO$_3$ and extracted twice with 25 ml ethyl acetate. The organic phases were combined, dried over MgSO$_4$, filtered and concentrated to dryness under reduced pressure to give 720 mg of crude amide ester (90% yield).

Example b)

A solution of 40 g trans acid ester (122 mmol, 1 equiv.) and 13.46 ml (1 equiv.) N-methyl-morpholine in 120 ml THF was added over 30 min to a cold (0-5° C.) solution of isobutyl chloroformate in 200 ml THF. After 60 min at 0-5° C. (the reaction is feed controlled so this hold time can be reduced), 24.95 g of the aniline (1 equiv.) and 5.23 g of lithium chloride (1 equiv.) were added. The reaction mixture was warmed to room temperature. After completion of the reaction (ca 3 h, in process control by HPLC), 280 ml water, 400 ml ethyl acetate and 400 ml HCl 1M were added. The organic phase was separated and extracted with 200 ml HCl 1 M. The aqueous phases were combined and the pH was adjusted to ca 9-10 by addition of 170 ml saturated aqueous Na$_2$CO$_3$ and extracted twice with 200 ml ethyl acetate. The organic phases were combined, dried over MgSO$_4$, filtered and concentrated at 45° C. under reduced pressure to give 54.2 g amide ester as a semisolid oil (84% yield, corrected for 2% residual ethyl acetate).

Step 7: Second Amide Coupling:

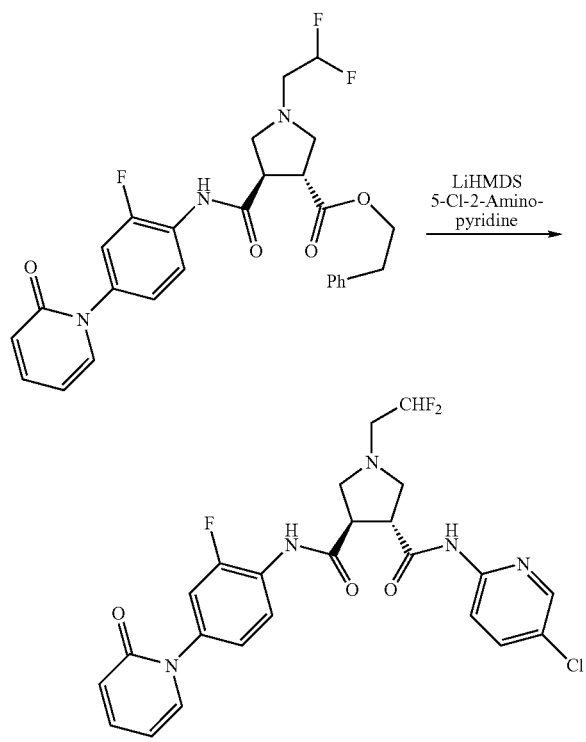

Example a)

197 mg 2-amino-5-chloropyridine (1.5 equiv.) and 500 mg amide ester (0.97 mmol, 1 equiv.) were dissolved in 4 ml THF. The solution was cooled to 0-5° C. 2.9 ml (3 equiv.) of 1M LiHMDS solution in THF was added over 5 min. After completion of the reaction (HPLC in process control), 2.5 ml 1M HCl were added over 15 min to quench the reaction and set the pH to 3.5. The biphasic mixture was extracted twice with 7.5 ml ethyl acetate. The organic phases were washed with 6.3 ml half saturated NaCl$_{aq}$, combined, dried over MgSO$_4$, filtered and concentrated to dryness under reduced pressure to give 720 mg of crude compound of formula (X).

Example b)

8.9 g 2-amino-5-chloropyridine (1.5 equiv.) and 25 g amide ester (45.3 mmol, 1 equiv.) were dissolved in 200 ml THF. The solution was cooled to 0-5° C. 136 ml of a 1 M LiHMDS solution in THF (3 equiv.) was added dropwise over 20 min. After 1 h reaction (HPLC in process control), the pH was adjusted to 3.5 by addition of 171 ml 2 M HCl$_{aq}$. The reaction mixture was extracted twice with 100 ml ethyl acetate. The organic phases were washed sequentially with 100 ml half saturated NaCl, dried over MgSO$_4$, filtered and concentrated at 45° C. under reduced pressure to give 34.8 g crude compound X. The crude product was dissolved in 260 ml ethanol and 260 ml heptane were added over 10 min. The clear solution was seeded. A suspension was obtained after ca 15 min. After 60 min at room temperature, 260 ml heptane were added over 30 min. The suspension was stirred 30 min at room temperature, 2 h at 0° C. and was filtered. The filter cake was washed with 50 ml of a cold (0-5° C.) 1:3 mixture of ethanol/heptane and was dried at 50° C. under reduced pressure to give 21.5 g compound X as a white powder (86% yield corrected for 3% residual heptane and 97.5a % HPLC, (S,S) enantiomer and cis isomer not detected by HPLC).

The cyclic anhydride can alternatively be prepared by the following sequence:

Step 1: [3+2] cycloaddition:

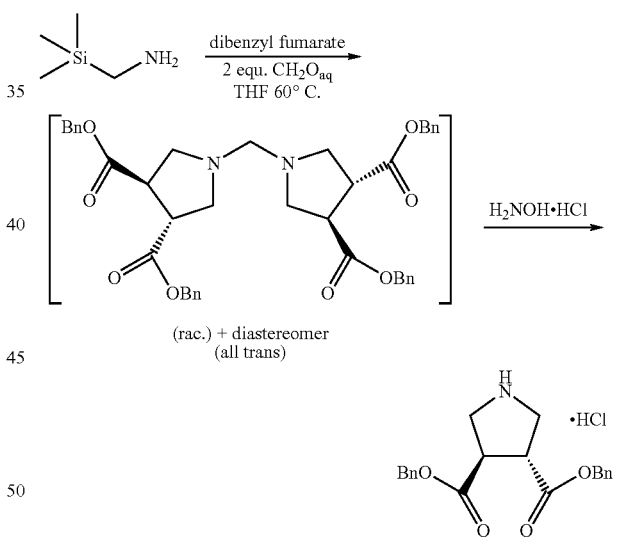

69.5 g (trimethylsilylmethyl)-amine (660 mmol, 1 equiv.) were dissolved in 765 ml THF. 99.7 ml 37% aqueous formaldehyde solution (2 equiv.) were added maintaining the temperature between 20-25° C. After 15 min stirring at room temperature, the resulting solution was added over 40 min to a refluxing solution of 200 g dibenzyl fumarate (1 equiv.) in 765 ml THF. After 20 h reaction, the reaction mixture was cooled to room temperature and was added over 10 min to a suspension of 52.3 g of hydroxylamine hydrochloride (1.14 equiv.) in 400 ml THF. The resulting clear solution was seeded upon which a turbid solution was obtained. The crystallization started rapidly. The white suspension was stirred 1 h at room temperature and was filtered over a P3 glass filter. The filter cake was washed with 72 ml water and twice with 400 ml MTBE. The crystals were dried at 50° C. under reduced pressure until constant weigh to provide 215 g of the pyrrolidine hydrochloride. (86% yield).

Step 2: Free Base Formation/Alkylation:

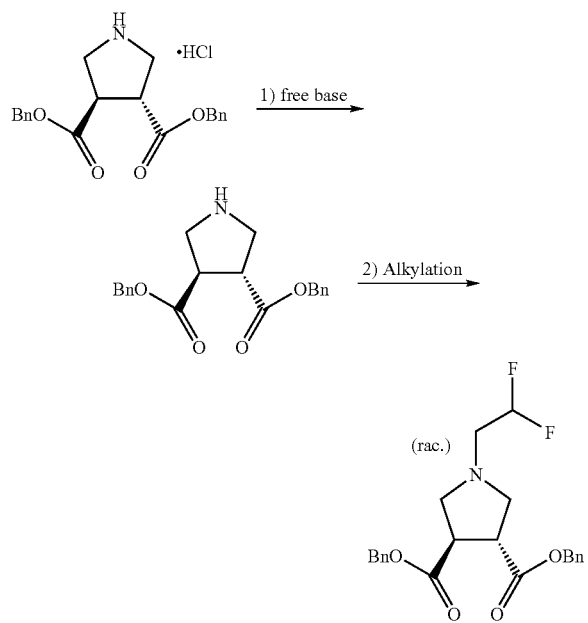

188.5 g hydrochloride (501.5 mmol, 1 equiv.) were suspended in 700 ml MTBE. 597 ml 1M NaOH were added at 0-5° C. The resulting clear biphasic mixture was separated and the aqueous phase (pH 13) was re-extracted with 350 ml MTBE. The organic phases were combined, dried over MgSO$_4$ and concentrated under reduced pressure at 40° C. to provide 166 g of a colorless oil (98% yield).

145 g of the resulting oil (427 mmol, 1 equiv.) were redissolved in 1.16 l acetonitrile. 114 g of difluoroethyl-3-benzenesulfonate (427 mmol, 1 equiv.) were added, followed by 87.8 ml ethyl-diisopropylamine (1.2 equiv.). The solution was heated at reflux during 24 h (>90% conversion), cooled to room temperature and concentrated under reduced pressure at 40° C. to a viscous orange oil. The crude mixture was dissolved in 750 ml AcOEt and washed with Na$_2$CO$_{3aq}$, NH$_4$Cl$_{aq}$ and water. The aqueous phases were re-extracted sequentially with AcOEt. The organic phases were combined, dried over MgSO$_4$, filtered, and concentrated under reduced pressure to give 178.5 g of crude product (80-85% m/m, >90% yield).

Step 3: Debenzylation:

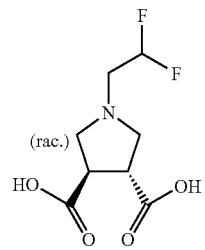

175 g of crude bis ester from previous step were dissolved in 1.6 l acetic acid and hydrogenated over 9.2 g 10% Pd/C at atmospheric pressure at 60° C. After completion of the hydrogenation, the reaction mixture was filtered at 60° C. The catalyst was washed with 175 ml hot (60° C.) acetic acid. The filtrate was cooled to room temperature and 800 ml MTBE were added resulting in a turbid solution. The solution was seeded and stirred 1 h at room temperature. 950 ml MTBE were added to the suspension which was then stirred overnight at room temperature, then 3 h at 0° C. The suspension was filtered and the filter cake was washed twice with 100 ml MTBE. The crystals were dried under reduced pressure at 60° C. to provide 89.7 g of product as a white powder (90% yield).

The crystallization in MTBE/AcOH is sensitive to the purity of the crude reaction mixture. Alternatively, the reaction mixture can be concentrated and the product crystallized in EtOH. (Re)-crystallization from water is also possible.

Step 4: Cyclic Anhydride Formation:

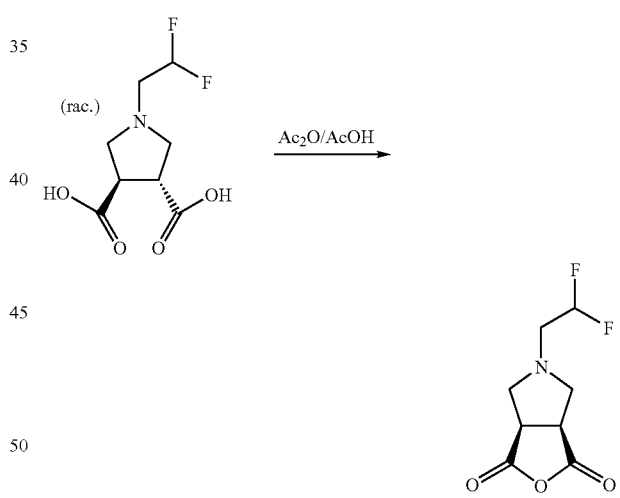

50 g (221 mmol, 1 equiv.) of bis acid were suspended in a mixture of 150 ml acetic acid and 24 ml acetic anhydride (1.15 equiv.) and heated at 105° C. After 1 h a clear solution was obtained. After completion of the reaction (ca 5 h, IPC by NMR), the reaction mixture was cooled to 50° C. and concentrated at 60° C. under ca 80 mbar to a volume of ca 40-50 ml (90 g solution). 400 ml t-amyl alcohol were added at 60° C. and the solution was concentrated to 150 g at 60° C. under ca 80 mbar (solvent exchange to t-amyl alcohol and removal of AcOH). The orange solution was cooled slowly to 40° C. upon which crystallization started. 300 ml heptane were added over 30 min at 40° C. The suspension was stirred overnight at room temperature and was filtered. The filter cake was washed with 100 ml heptane and dried under reduced pressure at 45-50° C. until constant weight to give 41 g of a light brown powder (ca 90% yield).

Alternative Preparation of the Bis Acid 33

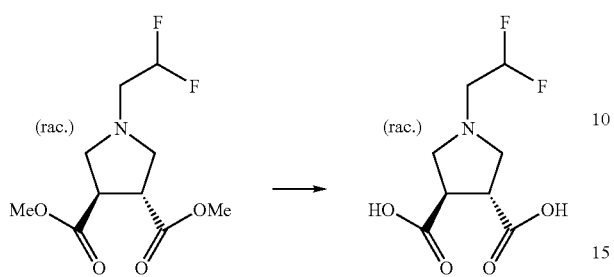

20 g of bis ester (74.75 mmol, 1 equiv.) were dissolved in a mixture of 40 ml THF and 20 ml water. 20.8 ml 32% $NaOH_{aq}$ (3 equiv.) were added and the reaction mixture was heated at 50° C. for 2 h (IPC by TLC, AcOEt/Heptane 3:1, visualization with $KMnO_4$). The THF was removed by distillation at 40° C. under reduced pressure. The aqueous phase was cooled to RT and washed with 20 ml AcOEt. Residual organic solvent in the aqueous phase were removed by distillation at 40° C. under reduced pressure. The aqueous phase was cooled to RT and the pH was adjusted to 3.5 by slow addition of 25% $HCl_{aq}$ (ca 27 ml) upon which the product crystallized. The thick suspension was stirred overnight at room temperature and filtered. The filter cake was washed with 20 ml cold (0-5° C.) water and dried at 50° C. under reduced pressure until constant weight to give 13.5 g of the expected bis-acid as a white powder (81% yield).

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. A compound of the formula:

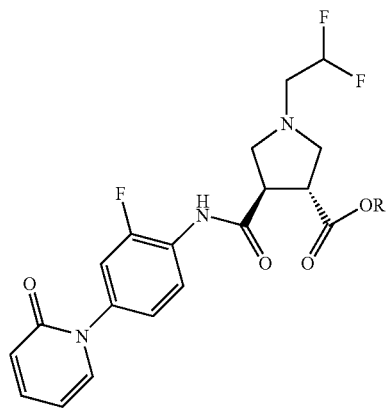

wherein R is phenylethyl, benzyl, cinnamyl, or a $C_{1-3}$ alkyl substituted by one or more substituents selected from the group consisting of hydroxyl, methoxy, ethoxy, and halogen.

2. A compound of claim 1, wherein R is phenylethyl.

3. A compound of claim 1, wherein R is benzyl.

4. A compound of claim 1, wherein R is cinnamyl.

5. A compound of claim 1, wherein R is a $C_{1-3}$ alkyl substituted by hydroxyl.

6. A compound of claim 1, wherein R is a $C_{1-3}$ alkyl substituted by methoxy.

7. A compound of claim 1, wherein R is a $C_{1-3}$ alkyl substituted by ethoxy.

8. A compound of claim 1, wherein R is a $C_{1-3}$ alkyl substituted by halogen.

* * * * *